(12) United States Patent
Munger et al.

(10) Patent No.: US 8,125,623 B2
(45) Date of Patent: Feb. 28, 2012

(54) CORRELATION TECHNIQUE FOR ANALYSIS OF CLINICAL CONDITION

(75) Inventors: Rejean Munger, Orleans (CA); Neil Lagali, Ottawa (CA)

(73) Assignee: Ottawa Hospital Research Institute, Ottawa (CA)

(*) Notice: Subject to any disclaimer, the term of this patent is extended or adjusted under 35 U.S.C. 154(b) by 272 days.

(21) Appl. No.: 12/383,930

(22) Filed: Mar. 30, 2009

(65) Prior Publication Data

US 2009/0303462 A1 Dec. 10, 2009
US 2012/0008130 A9 Jan. 12, 2012

Related U.S. Application Data

(63) Continuation of application No. PCT/CA2007/001706, filed on Sep. 21, 2007.

(60) Provisional application No. 60/827,605, filed on Sep. 29, 2006.

(51) Int. Cl.
*G01N 33/48* (2006.01)

(52) U.S. Cl. ......... 356/39; 356/301; 600/310; 600/323; 600/322

(58) Field of Classification Search .................. 356/39, 356/301–303, 432, 436; 600/310, 309, 322
See application file for complete search history.

(56) References Cited

U.S. PATENT DOCUMENTS

| | | | |
|---|---|---|---|
| 5,747,806 A | 5/1998 | Khalil et al. | |
| 6,040,578 A * | 3/2000 | Malin et al. | 250/339.12 |
| 6,718,189 B2 * | 4/2004 | Rohrscheib et al. | 600/310 |
| 6,928,311 B1 | 8/2005 | Pawluczyk et al. | |
| 6,965,793 B2 * | 11/2005 | Treado et al. | 600/476 |
| 6,975,891 B2 * | 12/2005 | Pawluczyk | 600/310 |
| 7,317,516 B2 * | 1/2008 | Treado et al. | 356/73 |
| 7,428,434 B2 * | 9/2008 | Tromberg et al. | 600/476 |
| 7,725,144 B2 * | 5/2010 | Ediger et al. | 600/310 |
| 7,890,158 B2 * | 2/2011 | Rowe et al. | 600/476 |
| 2002/0072658 A1 | 6/2002 | Rice et al. | |
| 2005/0075546 A1 | 4/2005 | Samsoondar et al. | |

(Continued)

FOREIGN PATENT DOCUMENTS

WO WO 93/16629 9/1993

(Continued)

OTHER PUBLICATIONS

Jensen et al., "Determination of urea, glucose, and phosphate in dialysate with Fourier transform infrared spectroscopy," Spectrochim. Acta., Part A 60, 899-905 (2004).

(Continued)

*Primary Examiner* — Layla Lauchman
(74) *Attorney, Agent, or Firm* — Dunlap Codding, P.C.

(57) ABSTRACT

The present invention provides a correlation technique for analysis of changes in bodily fluid and/or tissue in order to identify or monitor appearance, progression or treatment of a disease or condition in a subject. The disclosed method involves measuring spectral properties or changes in bodily fluid and/or tissue of a subject using at least two optical techniques; and correlating the measured properties or changes to a corresponding clinical condition or change in clinical condition, respectively. The measure of spectral changes over time can be used as indicators of changes in the clinical condition, for example, in disease treatment and/or disease regulation. This method is particularly useful for identifying a disease state and for monitoring efficacies of therapies used to treat different diseases or disorders, for example, renal dialysis.

25 Claims, 17 Drawing Sheets

U.S. PATENT DOCUMENTS

| | | | |
|---|---|---|---|
| 2005/0107676 | A1 | 5/2005 | Acosta et al. |
| 2005/0202567 | A1 | 9/2005 | Zanzucchi et al. |
| 2005/0222502 | A1 | 10/2005 | Cooper |
| 2009/0270702 | A1* | 10/2009 | Zeng et al. .................. 600/323 |

FOREIGN PATENT DOCUMENTS

| | | |
|---|---|---|
| WO | WO 99/43255 | 9/1999 |
| WO | WO 01/16577 | 3/2001 |

OTHER PUBLICATIONS

Vanholder et al., "New insights in uremic toxins," Kidney Int. 63, supplement 84, S6-S10 (2003).

Vanholder et al., "Uremic toxicity: present state of the art," Int. J. Artif. Organs 24, 695-725 (2001).

Jensen et al., "Online monitoring of urea concentration in dialysate with dual-beam Fourier transform near-infared spectroscopy," J. Biomed. Opt. 9(3), 553-557 (2004).

Eddy et al., "Near-infrared spectroscopy for measuring urea in hemodialysis fluids," Clin. Chem. 47(7), 1279-1286 (2001).

Olesberg et al., "Online measurement of urea concentration in spent dialysate during hemodialysis," Clin. Chem. 50(1), 175-181 (2004).

Mancini et al., "Continuous on-line optical absorbance recording of blood volume changes during hemodialysis," Artif. Organs 17(8), 691-694 (1993).

De Vries et al., "Continuous measurement of blood volume during hemodialysis by an optical method," ASAIO J. 38, M181-185 (1992).

Steuer et al., "Optical measurement of hematocrit and other biological constituents in renal therapy," Adv. Renal Repl. Ther. 6(3), 217-224 (1999).

Petrich et al., "Disease pattern recognition in infrared spectra of human sera with diabetes mellitus as an example," Appl. Opt. 39(19), 3372-3379 (2000).

Ge et al., "Identification of colonic dysplasia and neoplasia by diffuse reflectance spectroscopy and pattern recognition techniques," Appl. Spectrosc. 52(6), 833-839 (1998).

Lavine et al., "Genetic algorithms for spectral pattern recognition," Vibr. Spectrosc. 28, 83-95 (2002).

Lin et al., "Classification of in vivo autofluorescence spectra using support vector machines," J. Biomed. Opt. 9(1), 180-186 (2004).

Schneider et al., "Analysis of ecstasy tablets: comparison of reflectance and transmittance near infrared spectroscopy," Forensic Sci. Int. 134, 187-195 (2003).

Hale et al., "Optical constants of water in the 200 nm to 200μm wavelength region," Appl. Opt. 12(3), 555-563 (1973).

Cowe et al., "The use of principal components in the analysis of near-infrared spectra," Appl. Spectrosc. 39(2), 257-266 (1985).

Martinez et al., "On-line measurement of urea in blood using optical spectroscopy in the visible range; validation of the cell shrinkage hypothesis," IEEE Instrumentation and measurement technology conference ITMC 2004, Como, Italy, 1966-1969 (2004).

Soller et al., "Investigation of electrolyte measurement in diluted whole blood using spectroscopic and chemometric methods," Appl. Spectrosc. 57(2), 146-151 (2003).

Kim et al., "Data preprocessing and partial least squares regression analysis for reagentless determination of hemoglobin concentrations using conventional and total transmission spectroscopy," J. Biomed. Opt. 6(2), 177-182 (2001).

Goldfarb-Rumyantzev et al., "New empiric expressions to calculate single pool Kt/V and equilibrated Kt/V," ASAIO J. 48(5), 570-576 (2002).

Gabutti et al., "Unexpected haemodynamic instability associated with standard bicarbonate haemodialysis," Nephrol. Dial. Transplant. 18(11), 2369-2376 (2003).

Alam et al., "Measurement of pH in whole blood by near-infrared spectroscopy," Appl. Spectrosc. 53(3), 316-324 (1999).

Rosen et al., "Near-infrared spectrometric determination of blood pH," J. Surg. Res. 106(2), 282-286 (2002).

Valyi-Nagy et al., "Application of near infrared spectroscopy to the determination of haemoglobin," Clin. Chim. Acta 264, 117-125 (1997).

Kuenstner et al., "Measurement of hemoglobin in unlysed blood by near-infrared spectroscopy," Appl. Spectrosc. 48(4), 484-488 (1994).

Caspers et al., "Verification of the identity of pharmaceutical substances with near-infrared spectroscopy," Project 670400003, RIVM Report, Bilthoven, The Netherlands, (2002).

Meerwaldt et al., "Skin Autofluorescence, a Measure of Cumulative Metabolic Stress and Advanced Glycation End Products, Predicts Mortality in Hemodialysis Patients," American Society of Nephrology, pp. 3687-3693 (2005).

Mignani et al., "Spectral nephelometry for making extravirgin olive oil fingerprints," Elsevier Science, pp. 157-162, (2003).

De Vries et al., "Continuous Measurement of Blood Volume During Hemodialysis by an Optical Method," ASAIO Journal, pp. M181-M185, (1992).

* cited by examiner

CORRELATION TECHNIQUE FOR ANALYSIS OF CLINICAL CONDITION

CROSS REFERENCE TO RELATED APPLICATIONS

The present application claims priority to and benefit under 35 U.S.C. §119 as a continuation of International Application PCT/CA2007/001706, filed Sep. 21, 2007; which in turn, claims priority to the U.S. Provisional Application Ser. No. 60/827,605, filed on Sep. 29, 2006, the entire contents of International Application PCT/CA2007/001706 and U.S. Provisional Patent Application Ser. No. 60/827,605 are hereby expressly incorporated herein by reference.

FIELD OF THE INVENTION

The present invention pertains to the field of investigating clinical condition, or change in clinical condition and, more particularly, to a correlation technique investigating clinical condition of a subject using optical properties of bodily fluid or tissue.

BACKGROUND

Determining the concentration of an analyte or a marker of physical condition in a biological sample has been an important technique in the field of diagnostics. Markers that have diagnostic value include nutrients, metabolites, enzymes, immunity entities, hormones, and pathogens. The physical characteristics of a biological sample, such as temperature, optical properties, density, and hardness, are also of interest because they can provide indications with diagnostic value. Most determination methods currently in use to detect markers and analytes and many imaging methods employ signal-enhancing agents Current standard blood analysis (laboratory assay) is performed using blood samples obtained from a subject and assays are generally based on the identification of measurable features of the blood that are used to indicate the presence of a specific known species within the blood. In some instances the measurable features of the blood can be used to calculate the concentration of the known species in the blood. The presence of the species, or its concentration in the blood, is then used as an indicator or a marker and correlated to a certain state of health within an individual. Limitations of this approach of blood analysis include difficulties limitations are the long time needed to perform the various assays (in vivo and ex vivo) resulting in a historical snapshot of blood species as an indicator for dynamic and possibly rapid changing health states, and the reliance upon discrete, known species as adequate markers for health states within an individual.

Much interest has been expressed recently in developing spectroscopic, in particular visible, infrared (IR) or near-infrared (NIR) spectroscopic, techniques to non-invasively or minimally invasively determine blood or tissue chemistry or to analyze blood samples isolated from the patient. These non-invasive techniques have the advantage of eliminating or greatly reducing the need for collection of a blood sample or series of blood samples from a patient, which, in turn avoids the discomfort and complications that can be associated with blood collection. In techniques developed to date, the spectroscopic measurements are used to specifically identify or quantitate a particular marker or analyte, or combination thereof. For example, U.S. patent application Ser. No. 11/091, 396 (Publication No. 2005/0222502) discloses a respiratory monitoring apparatus that detects changes in physiological parameters relevant to respiration using near infrared spectroscopy. Similarly, U.S. patent application Ser. No. 11/125, 107 (Publication No. 2005/0202567) discloses a spectroscopic assay arrangement and technique for detection of the presence and/or concentration of an analyte in a sample of bodily fluid.

A number of patents and patent applications disclose spectroscopic methods and devices for non-invasive measurement of blood or tissue analytes (See, e.g., U.S. patent application Ser. No. 10/971,447 (Publication No. 2005/0107676), U.S. patent application Ser. No. 10/943,737 (Publication No. 2005/0075546), International PCT Application No. WO 01/016577, International PCT Application No. WO 99/043255, International PCT Application No. WO 93/016629 and U.S. Pat. No. 6,928,311). In each case, the techniques are used to specifically identify or quantitate a specific analyte or characteristic.

There remains a need, therefore, for a reliable, convenient method that permits measurement of the spectral properties of bodily fluid or tissue as an indicator of clinical condition, without the need to use the spectroscopic data to first identify and quantitate a specific analyte or characteristic, which is, in turn, used to extrapolate a clinical condition.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a correlation technique for analysis of bodily fluid or tissue of an individual. In accordance with an aspect of the present invention, there is provided a method for investigating the clinical condition of an individual, which method comprises the steps of: measuring spectral properties of bodily fluid or tissue of said individual using at least two optical techniques; and correlating the spectral properties to a corresponding clinical condition, wherein said spectral properties are measured in visible wavelengths, near-infrared wavelengths or both. In accordance with a specific embodiment of this aspect of the present invention, the method is used to investigate an individual's disease state.

In accordance with another aspect of the present invention, there is provided a method of monitoring changes in an individual's clinical condition comprising the steps of: measuring spectral changes in bodily fluid or tissue of said individual using at least two optical techniques; and correlating the measured changes to a corresponding change in clinical condition, wherein said spectral changes are measured in visible wavelengths, near-infrared wavelengths or both. In accordance with a specific embodiment of this aspect of the present invention, the method is used to monitor disease progression, onset, regulation or treatment in an individual.

In accordance with another aspect of the present invention, there is provided A method for deriving an index or indices for correlation to an observed clinical condition of a subject comprising the steps of: obtaining a body of raw spectral data by measuring spectral properties of bodily fluid or tissue of said subject using at least two optical techniques; and comparing the raw spectral data with the clinical condition of said subject.

In accordance with another aspect of the present invention, there is provided a method for overcoming confounding or interfering influences, such as oxygen saturation, hematocrit, hemoglobin, heparin, pH or environmental factors (e.g., temperature, humidity, etc.) on measured optical spectra by obtaining a body of raw spectral data from measured spectral properties of a bodily fluid or tissue of a subject using at least two optical techniques.

DETAILED DESCRIPTION OF THE INVENTION

Figure 1A:
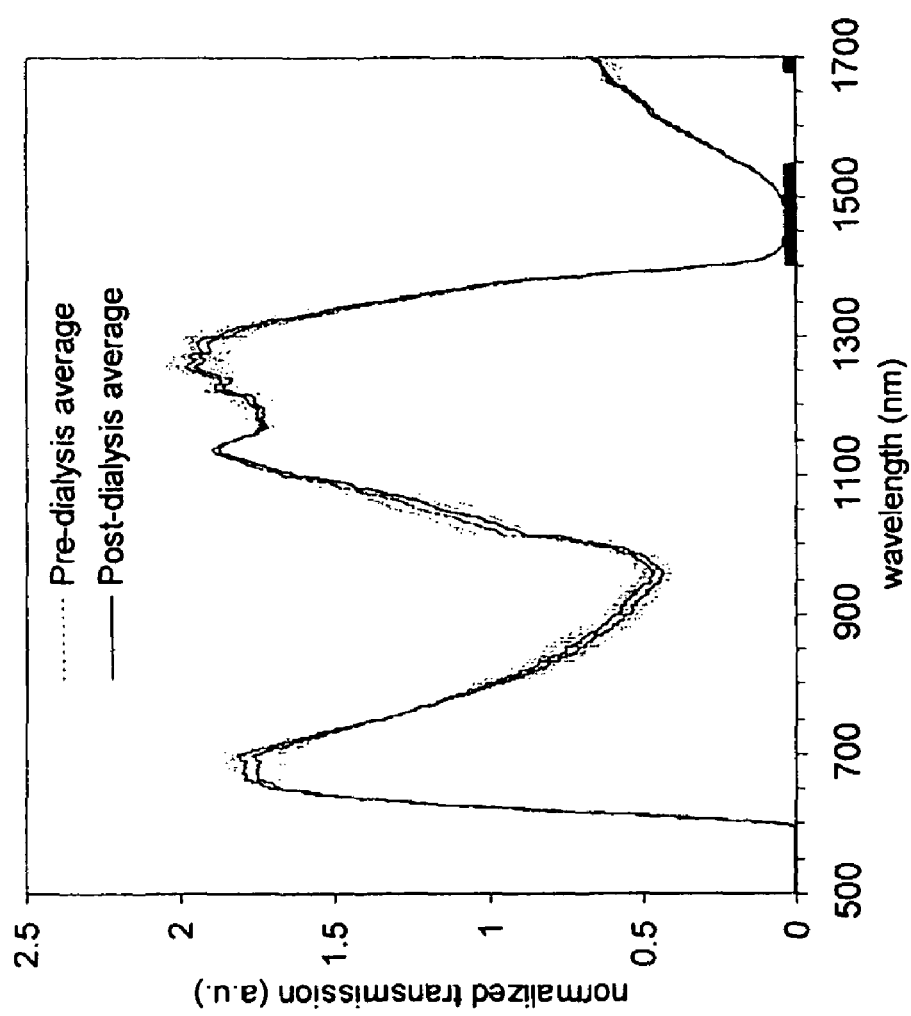
FIG. 1: Pre- and post-dialysis whole-blood spectra in linear normalized units for (a) transmission and (b) diffuse reflection modes. Blood spectra from individual patients are in gray, while average pre- and post-dialysis values (8 patients) are indicated by dashed and solid black lines, respectively. Shaded regions of the abscissa indicate wavelength ranges with signal-to-noise ratio <3 dB. Agreement between the published absorption spectrum of oxyhemoglobin (S. Prahl, "Optical absorption of hemoglobin," http://omlc.ogi.edu/spectra/hemoglobin/.) and the spectrum in (b) converted to logarithmic absorbance units is shown in (c).

The present application provides a method for measuring spectral properties of bodily fluid and/or tissue of a subject and using the spectral information to assess the state of health of the subject. The spectral properties are correlated to the patient's condition. In a specific example of the present invention, the subject's condition is a disease state, for example, from a well-understood clinical or medical condition.

The term "bodily fluid" as used herein, refers to any fluid of the body, including, but not limited to, sputum, saliva, whole blood, vitreous fluid, plasma, peritoneal fluid, cerebrospinal fluid and so forth.

The term "clinical condition" as used herein, refers to any condition of a human or animal that is effected by one or more an internal or external effector. Examples of internal effectors include, but are not limited to, genetic traits, congenital abnormalities and so forth. Examples of external effectors include, but are not limited to, pharmaceutical ingestion, food intake, exercise, stress, infection and so forth.

Since the method of the present invention involves the use of optical methods for detecting properties of the patient's bodily fluid and/or tissue, the method is amenable to non-invasive or non-contact uses. In addition, the method of the present invention allows for real-time, continuous measurements; in contrast to standard assay-based methods of blood analysis.

Spectroscopic Measurements

The measurements obtained using the method of the present invention are relative and are not chemical-specific. Therefore, difficulties associated with absolute calibration of absorption and scatter, corrections for subject variability, and developing a spectral library associated with known chemical entities are largely circumvented. A further advantage of this approach is its suitability for the detection of signatures from complex treatment-initiated biochemical events in vivo, which involve either too many molecules to isolate and quantify (even for invasive techniques), involve unknown molecules and interactions, or are rendered undetectable outside of a living body.

In general, the method of the present invention comprises the steps of illuminating bodily fluid and/or tissue of a patient (in vivo or ex vivo) with light and obtaining at least two optical measurements based on two distinct light-fluid or light-tissue interaction phenomena. For example, the method of the present invention can make use of a combination of any two of the following phenomena: diffuse reflection, inelastic (Raman) scattering, absorption/transmission, or fluorescence.

In accordance with a specific embodiment of the present invention, the illumination light used in the method of the present invention is in the visible and/or near infrared spectrum of radiation (i.e., in the range of 400-2500 nm). Alternatively, the illumination light can include light in the UV and mid-IR regions, such that the full illumination spectrum range can span 300 nm to 30 microns A specific example of an optical measurement of light-tissue interaction is the measurement of tissue autofluorescence, for example, as described by Meerwaldt, et al. (2005) J. Amer. Soc. Nephrology 16:3687-3693. The measured optical properties are then correlated to a known clinical condition or a change in clinical condition by comparison to optical properties known to be associated with certain conditions or by comparison to optical properties measured over time, respectively.

By making use of two distinct light-fluid or light-tissue interaction phenomena, the ability to correlate bodily fluid or tissue optical changes to a clinical condition or a change in clinical condition is improved in comparison to the use of a single light-fluid or light-tissue interaction phenomena. In particular, there is an increased robustness and sensitivity associated with the use of at least two light-fluid or light-tissue interaction phenomena in comparison to the use of one such phenomena.

Spectral information from bodily fluid and tissue can be obtained using various spectrometric techniques and, as would be appreciated by a worker skilled in the art, such techniques can be used in the method of the present invention. The goal is to obtain wavelength dependent measures of the interaction of light with the bodily fluid or tissue of interest. For example, a broad spectrum source (all wavelengths in the source) can be used to illuminate the bodily fluid or tissue of interest. A dispersive element, (for example a diffraction grating or a prism) can be used to separate the different wavelengths of light returning from the sample and collect the intensity at each wavelength on a detector, digital or analog. Alternatively, sources of different wavelengths can be used to illuminate the bodily fluid or tissue of interest, followed by measurement of the intensity of light returning after the light/tissue interaction has occurred. Possible detector types could be but are not limited to, Photomultiplier tubes, diode arrays, Charge Coupled Devices, cmos detectors photographic film and any type of photodiode including avalanche photodiodes. Example of light sources include, but are not limited to, arc, incandescent or fluorescent lamps, optionally in combination with one or more optical filters, any of the many kinds of light emitting diodes, any of the many kinds of lasers, and natural light.

In vivo work requires that the possibility of light damage to the tissue during measurements be minimized or avoided altogether. Thus, in practicing present invention in vivo the light intensities employed should be below the threshold for tissue damage as per published standards. It is then possible that the intensity of light returning from the tissue will be low. To overcome these problems certain embodiments of the method of the present invention include an additional step or steps to improve signal to noise ratio. Suitable techniques for use in the method of the present invention include, but are not limited to, lock-in detection strategies as well as, analog and digital filtering techniques. In lock-in detection strategies, the illumination source intensity is modulated using a well controlled pattern. The detection system is simultaneously synchronized to the modulation pattern. The result is that only signal modulated with the same pattern as the source is optimally detected, other signals (i.e., the noise) are not efficiently detected and, thus, the noise signal is reduced, improving the signal quality. Filtering techniques, whether analog or digital, can be used to selectively remove signals that are assumed (based on expected responses of the system) to contribute mostly to noise. An analog implementation would filter the signal using an electronic circuit and a digital technique using post acquisition algorithms.

In accordance with certain embodiments of the present invention the method includes an enhancement technique to maximize the signal-to-noise ratio. For example, positive correlation filters at the light source output can be used to provide optimum illumination of only those wavelengths contributing significantly to the spectral variables of interest, thereby allowing increases in illumination power at these wavelengths, further increasing sensitivity (U.S. Pat. No. 5,747,806). The demonstration of chemical-specific detection through the retinal blood (U.S. Patent Application No. US2002/0072658)—a more demanding approach—provides further evidence that the method of the present invention has sufficient sensitivity to detect small changes in the presence of confounders in the eye and in the blood.

A broad range of probe wavelengths as separate or combined probes for both absorbed and scattered light are available for use in the method of the present invention. This permits very sensitive detection of evidence of effects in the bodily fluid and/or tissue using the method of the present invention. Since the method of this invention is not substance-specific, many of the specificity issues encountered with previous methodologies are minimized or avoided.

The poor reproducibility in the measurements obtained using previous methods can be readily minimized or avoided using the method of the present invention. Spectral fluid and tissue fluctuations can be large and random even during baseline measurements or in measuring a control group. In such instances, however, lower wavelength resolution can be implemented through binning procedures, or a single measurement of absorption or scatter alone may be used to reduce variability. Inter-treatment and inter-patient variability is not a concern when using the method of the present invention to monitor disease progression, regulation or treatment, due to the relative nature of the measurement approach. Furthermore, patient-specific measurements and algorithms can be employed in the present method, wherein certain wavelength regions of prognostic or diagnostic value may only apply to a specific individual or small group of individuals.

In accordance with one embodiment of the invention the measured spectral properties are compared to the spectral properties of a known population as an indicator or measure of a similarity or difference in clinical condition of the subject under study in comparison to the average clinical condition of the known population. This technique is useful for diagnostic applications as well as for research applications.

In accordance with one embodiment of the invention changes in the spectral properties are monitored over time, relative to baseline measurements, as an indicator of a change in clinical condition over time and, for example, with the addition, removal or change in one or more internal or external effectors. With appropriate correction of baseline shifts and drift, spectral changes over time can be used, for example, as indicators of treatment and disease regulation, as opposed to the hitherto isolative approach of chemical-specific detection. This technique is useful for diagnostic applications as well as for research applications. In research, the emphasis is elucidation of blood properties and/or changes related to treatment-physiology interactions in a well-known clinical situation, rather than diagnostic capability.

In accordance with this embodiment of the present invention, the steps of illumination and optical property measurement are repeated at discrete time intervals in order to monitor changes in clinical condition over time, for example, when monitoring changes in disease state in response to therapy. The selection of the time intervals for testing is well within the abilities of a worker skilled in the art and is made based on the specific application of the method, taking into consideration, for example, the disease or condition afflicting the patient, the type of treatment, the length of treatment or the uptake and/or metabolism of a pharmaceutical used in the treatment.

In an alternative of this embodiment of the present invention, changes in optical properties are measured by continuous real-time monitoring of the optical properties of a subject's bodily fluid and/or tissue.

Irrespective of whether the spectral changes over time are obtained using discrete time samples or continuous real-time monitoring, the spectral changes are subsequently correlated to a change in the clinical condition of the subject, for example, a change in disease state.

Data Processing

After the raw optical spectra are obtained, they are processed in order to separate and emphasize features within the spectra correlated to a clinical condition, while minimizing those features arising from instrumental artifacts and undesired physical effects (sources of noise). As indicated above, multiple techniques (i.e., absorption, scatter, fluorescence) can be used according to the present invention to obtain the initial spectral information. The optical parameters that correlate to a particular clinical condition or change in clinical condition can be selected from the entire data set of spectral information from the multiple techniques (following the application of techniques such as multivariate analysis), using well established or new methodologies specific to the application.

In accordance with one embodiment of the present invention, the analysis used to process the raw optical absorption and scatter spectra combines the principles of spectral nephelometry (Mignani, A. (2003) "Spectral Nephelometry For Making Extravirgin Olive Oil Fingerprints" *Sensors and Actuators* 90: 157-162) with the methods of chemometric analysis used in NIR absorption spectroscopy (Caspers, P. (2002) "Verification of the identity of pharmaceutical substances with near-infrared spectroscopy" Bilthoven, The Netherlands, National Institute of Public Health and the Environment). This approach comprises the following features:

- normalization of spectra relative to baseline sample (bodily fluid/tissue or pre-treatment measurement);
- normalization relative to total integrated power (where spectral shape is desired instead of absolute intensity information);
- combination of chosen spectral bands and possible aggregation of absorption and scatter spectra;
- application of spectral pretreatments: baseline correction, standard normal variate transformation, multiple scatter correction, wavelength selection, smoothing, derivatives, etc. (Caspers, P. (2002) "Verification of the identity of pharmaceutical substances with near-infrared spectroscopy" Bilthoven, The Netherlands, National Institute of Public Health and the Environment); and
- application of a chemometric algorithm.

Advantageously, based upon the applicants' experience and good results obtained in the literature, the chemometric technique of principal component analysis (PCA) (Cowe, I. (1985) "The Use of Principal Components in the Analysis of near-infrared spectra," *Applied Spectroscopy* 39(2): 257-266) can be used as the chemometric algorithm. PCA is a widely used multivariate analysis technique that enables the expression and visualization of complex spectra in terms of the independent elements responsible for variation within the spectra. Many other techniques such as, but not limited to, Linear Discriminant Analysis or non-linear models of spectral compositions can be used to summarize the data into a small number of clinically relevant indices/parameters.

In accordance with one embodiment of the present invention, the method is used in a clinical setting. In one example of such a clinical implementation, the values of the indices/parameters extracted from the spectral analysis can be compared to benchmark values for these indices. The benchmark values can be from an earlier time point for the same patient (to quantify changes in the patient's health) or based on data obtained from a human population (to identify patient(s) that could have a particular clinical condition, for example, a disease state).

Applications of the Method

The method of the present invention has broad application to any situation in which it is desirable to identify, or monitor changes in, the clinical condition of a subject. In general, the method takes advantage of the fact that the optical properties of bodily fluid and/or tissue changes over time or due to the presence, absence or change of an external or internal effector (e.g., disease, drug ingestion, infection, change in health status, etc.). For example, measurement of the optical spectrum of bodily fluid and/or tissue and comparing to spectra of bodily fluid and/or tissue of individuals known to be either affected or unaffected by the external factor allows correlation to a particular clinical condition affected by the presence or absence of the external factor. As a further example, measurement of the optical spectrum of bodily fluid and/or tissue of a subject at various points in time allows the determination of changes in spectral response from the bodily fluid and/or tissue that are highly correlated to a change in clinical condition. The spectra obtained from the subject under study can be compared to standard spectra obtained using a standard reference method, or can be analyzed based on medical opinion or subjective assessment in situations in which no standard is available. In the latter case, the observed change in the optical properties of the bodily fluid and/or tissue can be correlated with a change in the observed change in, for example, symptoms of the subject.

The external factor may or may not be an identified chemical species. Where no species is known or where numerous species may be involved in a particular clinical condition, the correlation technique of the present invention is particularly useful as it correlates bodily fluid and/or tissue changes directly with the external or internal factor, bypassing the isolation/identification of candidate species.

In accordance with certain embodiments of the present invention, the method is used either as an alternative or a supplement to standard clinical and laboratory analyses.

In accordance with particular embodiments of the present invention, the method is used as part of a routine health assessment of an individual. For example, the present method can be used to verify the absence/presence of a clinical condition or monitor changes in a clinical condition, such as a disease, during the course of treatment (physical, pharmaceutical or other). In embodiments, the present method can be used to monitor the course of treatment of clinical conditions or diseases including but not limited to: diabetes, cancer, heart disease, and end-stage renal disease. The method of the present invention is also amenable to medical testing such as may be employed during surgery (such as online monitoring during cardiopulmonary bypass), as part of at-home monitoring, during therapeutic treatment (such as online monitoring during renal dialysis, physiotherapy, chemotherapy or radiation therapy), or hospital bedside monitoring or other point-of-care monitoring.

It should be readily understood that the method of the present invention can be used to correlate optical properties with a clinical condition, such as disease, as the endpoint of the method, and, to correlate optical properties to clinical outcomes, prediction of outcome, or prediction of response to treatment (in the case of therapeutic applications). Alternatively, the method of the present invention can be used to investigate spectral changes to eventually isolate bodily fluid or tissue factors to develop new biomarkers and/or interventions.

It should be readily appreciated that the method of the present invention is not limited to medical applications. Rather, the method can be used to monitor or identify any perturbation of an individual's condition, such as in response to a particular stimulus. By way of example, the method can be used for monitoring athletic conditioning, dieting, response to stress, etc.

The method of the present invention can also be used to monitor individuals at risk, or at high risk, for developing certain clinical conditions such as diabetes, cancer, and heart disease. By monitoring changes in the optical properties of an individual's bodily fluid and/or tissue it can be possible to facilitate early detection of the onset of disease, which, in turn, will permit early treatment or prevention. Similarly, since the method of the present invention is sensitive to molecular and biochemical changes in an individual, it can be used as a research or diagnostic tool to identify changes in the optical properties of bodily fluid and/or tissue that can then be used as an early step in the search for the root cause of observed changes in the clinical condition of the individual.

In accordance with a specific embodiment of the present invention, the method is used to monitor known bodily fluid (e.g., blood) components, or total bodily fluid and/or tissue changes in response to a stimulus (irrespective of whether or not there is any knowledge of the relevant components).

To gain a better understanding of the invention described herein, the following examples are set forth. It should be understood that these examples are for illustrative purposes only. Therefore, they should not limit the scope of this invention in any way.

EXAMPLES

Example 1

Hemodialysis Monitoring In Whole Blood Using Transmission and Diffuse Reflection Spectroscopy 1. Introduction Hemodialysis is a medical treatment that involves diffusive and convective removal of solutes and water from the blood of patients with end-stage renal disease (ESRD), whose kidneys can no longer perform this task. Current standard measures of treatment adequacy and dose of hemodialysis are based upon the clearance of the low molecular weight compound urea from the blood, determined from pre- and post-dialysis blood samples analyzed in a clinical laboratory. While measurement of urea clearance is the most widely used method to assess dialysis adequacy in ESRD, urea is only one of many metabolites that accumulate in ESRD and it may represent a surrogate marker rather than a principal toxin[1-3]. While the hemodialysis procedure filters the blood of low-molecular weight water-soluble molecules, a host of potentially toxic middle- and high-molecular weight molecules remain unfiltered. These include protein-bound molecules that may contribute to the development of complications in ESRD patients, such as the uremic syndrome and vascular disease[3]. Investigation of uremic toxins is clearly of critical importance in developing treatment strategies that improve patient quality-of-life and longevity.

One means of achieving this goal is to identify, classify and characterize the clinical importance of as many candidate toxic molecules as possible, as is the mandate of the European Uremic Toxin Work Group (EUTox) initiated in 2000[4]. As a consequence, however, of the complexity and the limited understanding of the chemistry of kidney disease and its treatment, it has proven difficult to find individual analytes (isolated from the rest of the blood chemistry) that can accurately and reliably describe the disease state or report the efficacy of treatment. An alternative approach is to monitor whole blood as a complex structure and correlate any changes in this structure to the hemodialysis treatment and the patient's clinical status or condition. The emergence of consistent patterns of change or absence of change in blood properties could lead to new candidate toxicity indicators and to the subsequent investigation of factors underlying the observed patterns. An advantage of this latter approach is the simultaneous inclusion of numerous molecules including their interactions and indirect effects as they contribute to the observed blood properties. In this regard, optical spectroscopy can be an effective tool to probe the complex response of blood to treatment in the clinic.

Several approaches using optical spectroscopy to monitor hemodialysis treatment have been reported. These studies utilize light as a non-contact tool for reagentless determination of urea and other solute concentrations in spent dialysate fluid[2,5-7]. Although such approaches are useful for online monitoring of filtered analytes, the direct optical detection of analytes retained in blood (including unfiltered compounds) has not been reported. While whole blood optical monitoring during hemodialysis has been achieved, the reported methods have used a small number of discrete wavelengths to monitor specific blood parameters such as hematocrit, blood volume, oxygen saturation and hemoglobin levels[8-10]. These parameters, however, are not indicative of potential toxins within the blood nor do they provide a means to assess the efficacy of treatments.

The present study demonstrates that features in the optical spectrum of undialyzed versus dialyzed whole blood showed a significant difference as a result of the hemodialysis treatment. Additionally, the detected changes in the spectrum of whole blood were found to be consistent with accepted clinical outcomes, as determined by comparing the spectroscopic results to clinically-measured analyte changes (as a gold standard) following dialysis treatment. While the optical monitoring techniques used are readily adaptable for online monitoring, the whole-blood approach can enable be used to identify surrogate markers for toxicity or for patient prognosis through established disease pattern recognition techniques[11-14].

2. Materials and Methods 2.1. Clinical Design

A sample population of eight ESRD patients undergoing regular hemodialysis treatment (four-hour sessions, three times a week) was recruited on a volunteer basis for the pilot study.

Volunteers represented a broad cross-section of ESRD patients in terms of age and gender (6 male, 2 female; mean age 61.5 years; age range 39-75 yrs), time since initiation of dialysis (18 mos. to 284 mos.) and the presence of other systemic conditions (hypertension—3 patients, Type-II diabetes—3 patients). Blood extraction from subjects occurred immediately before and after a single hemodialysis treatment (<1 min). The day of blood extraction coincided with the monthly laboratory blood testing day for each volunteer, thereby allowing subsequent correlation of spectral data to clinical laboratory results.

2.2. Blood Sample Preparation

Samples of whole blood for the study were obtained at the same time standard clinical blood samples were obtained. Blood was drawn into standard 3 ml purple-top collection tubes containing 5.4 mg $K_2$-EDTA as an anticoagulant. The collection tubes were manually agitated to provide a homogeneous suspension and 1 ml from each tube was transferred to an optical cell and sealed. The delay between sample collection and the start of optical measurements averaged one hour, with a maximum delay of two hours. To test the influence of the delay, optical spectra from a single blood sample were taken hourly over a four hour period at room temperature, with no significant change observed in the spectra (data not shown).

Serum urea and potassium levels were quantified using an automated Beckman Coulter LX20 analyzer. Manufacturer-supplied reagents were used and an indirect ion selective electrode method was used to quantify potassium while a coupled enzymatic rate method was used for urea. The intra-assay variability of these techniques is nominally accepted to be approximately 2% (coefficient of variation).

2.3. Measurement of Transmission and Diffuse Reflection Spectra

Optical cells with a 2 mm optical path length were used, made from optical glass with >80% transmission over the wavelength range 365 nm-2500 nm (Varsal Inc.). For measurements, the optical cells were placed in a custom sample holder ensuring both repeatable cell placement and minimal optical-mechanical interference to avoid stray light and spurious reflections. A focused spot (4 mm diameter) from a current-stabilized 20 W tungsten-halogen light source (model ASB-W-020, Spectral Products, Inc.) was used to illuminate the optical cell. Light transmitted through the cell was focused into a collection optical fiber (400 µm core diameter low-OH fiber, Ocean Optics Inc.) connected to a spectrometer. Light backscattered in a cone over a 10°-30° angle relative to the incident beam was captured by a wide-aperture achromatic lens and focused to a second collection optical fiber (600 µm core diameter low-OH fiber, Ocean Optics Inc.) connected to a spectrometer. The off-axis geometry used for backscatter collection minimized the interference of both specular reflection and edge effects from the optical cell.

Optical spectra were acquired over the 400 nm-1700 nm region using two spectrometers spanning wavelength ranges of 400 nm-1000 nm (model SD2000, Ocean Optics Inc., 2048-element silicon photodiode array; spectral resolution 0.33 nm) and 900 nm-1700 nm (model InGaAs512, StellarNet Inc., 512-element InGaAs photodiode array; spectral resolution 2.25 nm). Spectra were acquired through computer control with acquisition times of 8 ms and 800 ms for transmission and diffuse reflection, respectively, for the near infrared spectrometer, and 10 ms for both modes using the visible/near infrared spectrometer.

Blood samples were maintained at room temperature and sample heating was minimized by using a mechanical shutter kept open only during the spectral acquisition period. Three data sets were obtained for each sample, where for each set the cell was removed, agitated and replaced. The three spectra were subsequently area-normalized and then averaged to account for sources of variation resulting from optical cell placement and variations in light intensity level. Prior to averaging, the maximum coefficient of variation among any set of three normalized spectra was 2% and 9% for wavelengths below and above 1000 nm, respectively. All subsequent analyses reported here were performed using normalized, averaged spectra. Influences of the spectral properties of the light source, the optical cell, and optical elements in the light delivery and detection paths were removed by dividing the normalized transmission and diffuse reflection spectra by a reference measurement taken with an empty optical cell (transmission path) and a broadband mirror placed behind an empty optical cell (diffuse reflection path).

About 1 W of focused optical power was delivered to the blood sample. Typically about 15% of the incident light was transmitted through a sample while about 5% was diffusely reflected in the direction of the detection cone. Although the transmitted and diffusely reflected light levels were high, signal-to-noise ratio was reduced due to manual attenuation of the delivered and/or detected light streams which was necessary to accommodate both a limited photodetector dynamic range and a requirement for the simultaneous measurement of transmitted and diffusely reflected paths with differing light levels. Wavelength regions where optical signal-to-noise levels failed to exceed an imposed 3 dB minimum threshold were identified and excluded from subsequent analyses. Of particular note, strong water absorption in the 1400-1550 nm band resulted in a high dynamic range detection requirement and therefore a reduced signal-to-noise ratio.

3. Data Analysis and Interpretation

3.1. Whole Blood Spectra

Figure 1B:
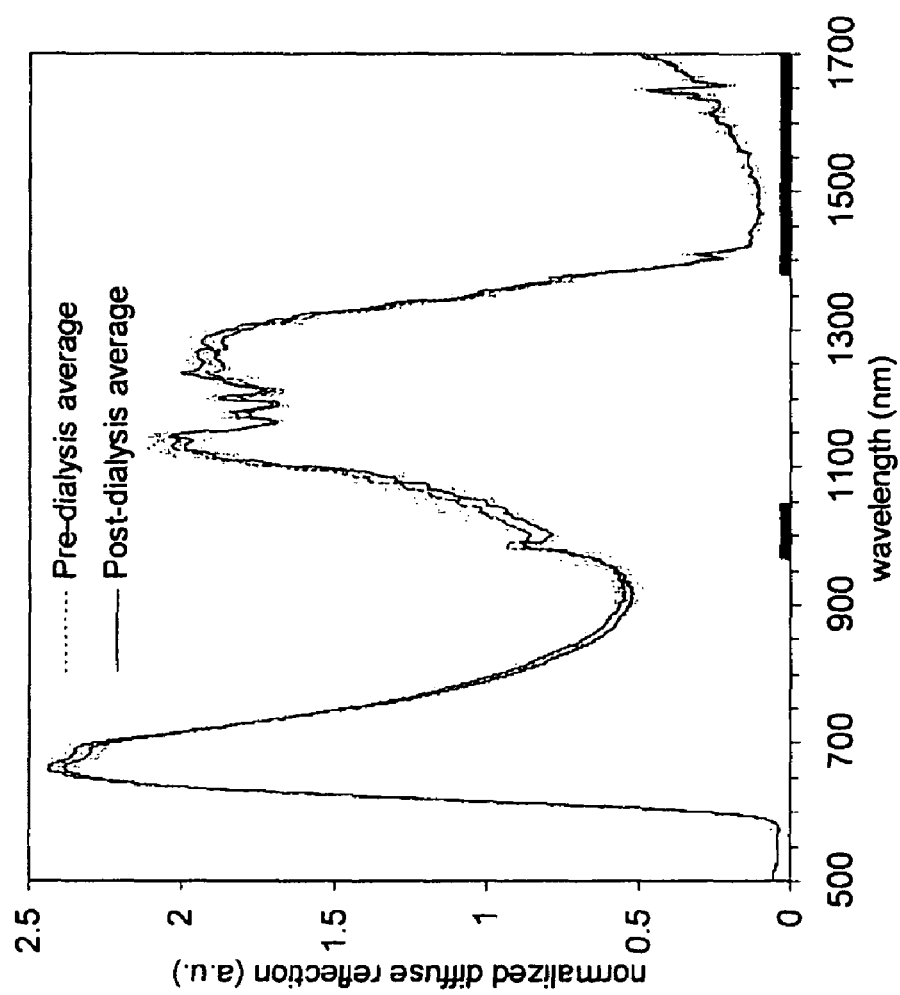
Figure 1C:
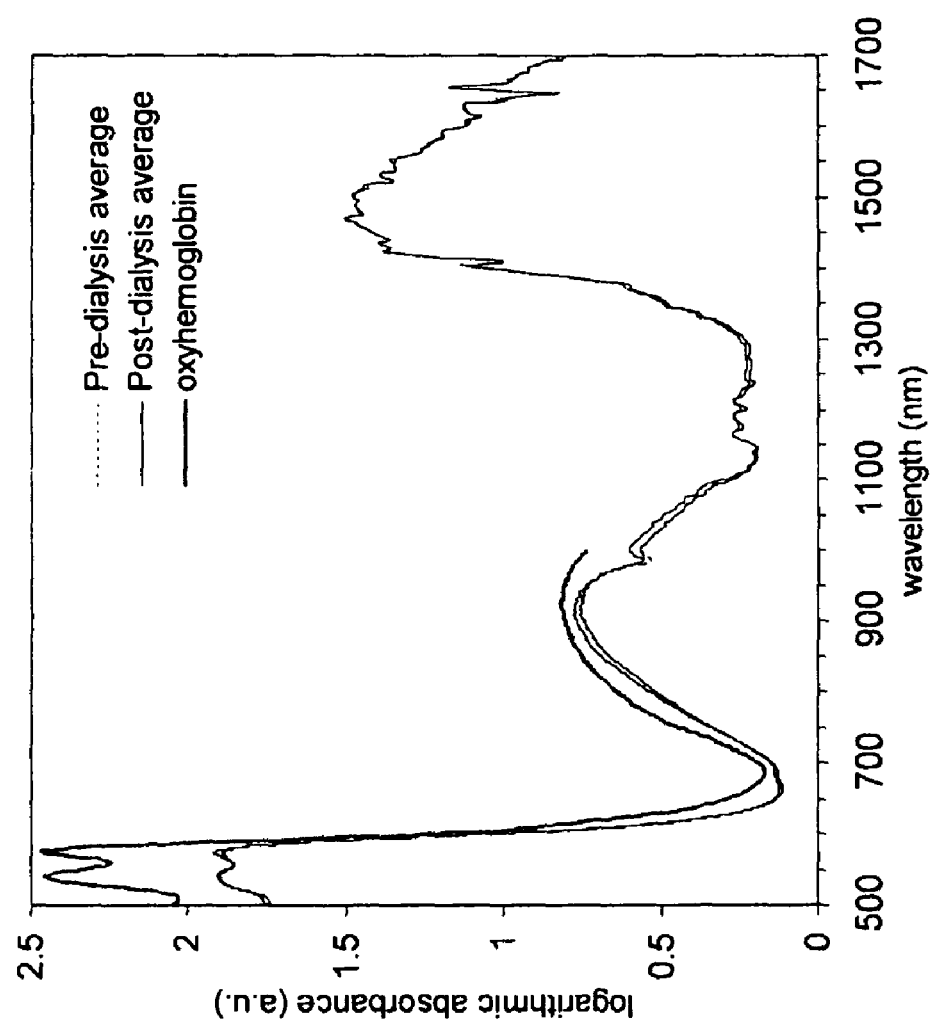

Thirty-two separate spectra were obtained; these corresponded to pre- and post-dialysis blood for 8 patients in both transmission and diffuse reflection modes, FIGS. 1(a) and (b). The spectra differed depending upon the light interaction mode, which is consistent with results reported elsewhere[15]. In FIG. 1(c) the data in FIG. 1(b) was plotted as an absorbance along with published absorption data for pure oxyhemoglobin[16]. Good agreement was observed between the measured and published results, and in particular the characteristic double-peaked absorption of oxyhemoglobin was visible, with peaks at 542 nm and 575 nm. Hemoglobin (principally its oxygenated and deoxygenated forms) dominates whole blood absorption of wavelengths shorter than 1000 nm, whereas water generally dominates absorption above 1000 nm. The well-known broad absorption peaks of water centered at 970 nm and 1440 nm and a minor peak at 1200 nm were also visible in the measured spectra in FIG. 1(c)[17].

Other than area-normalization, averaging, and referencing, the spectra were not filtered, smoothed, derivatized or pre-treated prior to analysis. In this manner the detailed fluctuations characteristic of turbid media were preserved and permitted the interpretation of raw spectral changes in whole blood independent of data processing methods.

3.2. Intra-Group Comparison

To assess the significance of spectral changes observed as a result of hemodialysis, quantitative analysis of full-spectrum change was performed using the principal component analysis (PCA) method[18]. Briefly, in the PCA method a group of input spectra were mathematically decomposed into a small set of uncorrelated, orthonormal variables (the principal components) which account for the major sources of variation across the group of spectra. Moreover, for each individual spectrum it was possible to derive a set of principal component 'scores' or 'weights' representing the contribution of each principal component to the linear decomposition of each spectrum in terms of the principal components. By limiting the analysis to only the most significant sources of variation among the spectra, an entire optical spectrum can be represented by one or a few variables.

PCA was performed separately for transmission and diffuse reflection using the two groups of 16 whole blood spectra shown in FIG. 1. Eigenvalues corresponding to the first principal component had a value greater than 1, and therefore only the first principal component was retained as an indicator of the most significant source of variation among the 16 optical spectra. The first principal component accounted for 94% and 63% of the variation in the transmission and diffuse reflection spectra, respectively. Scores for the first principal component for the spectrum of each patient are given in Table 1. Mean values for each group (pre- or post-dialysis) are shown along with the corresponding results of a paired t-test for the null hypothesis (no spectral difference due to treatment). For both light interaction modes the null hypothesis could be rejected, indicating significant whole-blood spectral changes in transmission ($P<0.003$) and diffuse reflection ($P<0.001$) due to hemodialysis treatment.

TABLE 1

Principal component scores used to test the null hypothesis of no difference between pre- and post-dialysis blood based on full-spectrum analysis.

| | First Principal Component Scores | | | |
|---|---|---|---|---|
| | Transmission | | Diffuse reflection | |
| Patient | Pre | Post | Pre | Post |
| 1 | −13.19 | −13.82 | 9.54 | 10.96 |
| 2 | −10.68 | −11.78 | 7.72 | 9.68 |
| 3 | −14.51 | −16.03 | 9.84 | 11.16 |
| 4 | −11.04 | −13.20 | 9.23 | 11.08 |
| 5 | −11.35 | −11.73 | 7.60 | 8.36 |
| 6 | −12.48 | −14.84 | 9.74 | 11.77 |
| 7 | −14.54 | −15.05 | 10.35 | 10.75 |
| 8 | −14.21 | −15.41 | 10.16 | 11.30 |
| Mean | −12.75 | −13.98 | 9.27 | 10.63 |
| paired t | 4.69 | | −6.59 | |
| P | 0.0022 | | 0.0003 | |

Figure 2A:
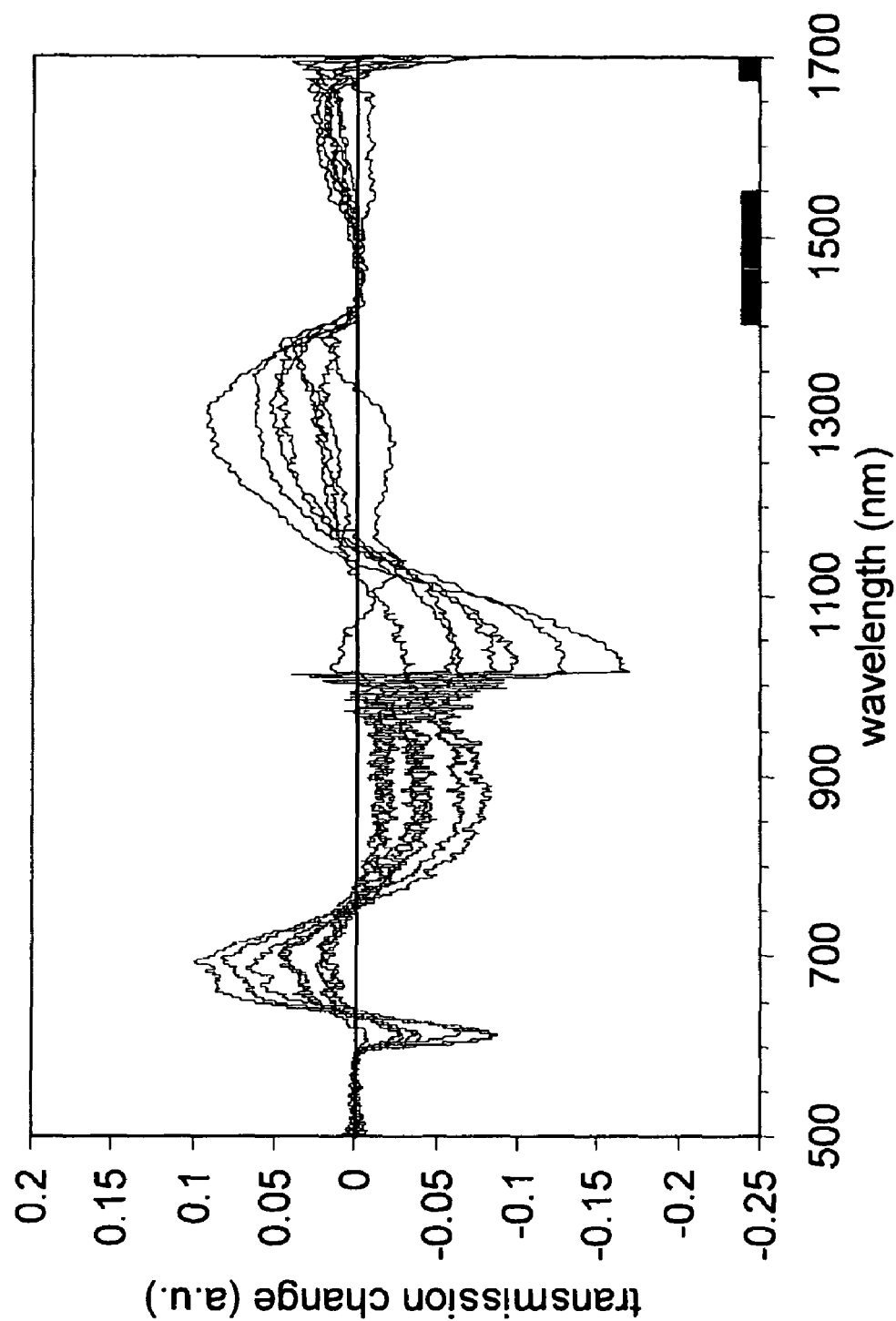
FIG. 2: Whole blood difference spectra (post-dialysis—pre-dialysis) for 8 patients (each line is for a single patient) in (a) transmission and (b) diffuse reflection modes. A horizontal line at zero-change is included for reference. The discontinuities at 1015 nm (transmission) and 980 nm (diffuse reflection) are due to concatenation of spectra obtained from two different spectrometers, while shaded regions of the abscissa indicate <3 dB signal-to-noise ratio.
Figure 2B:
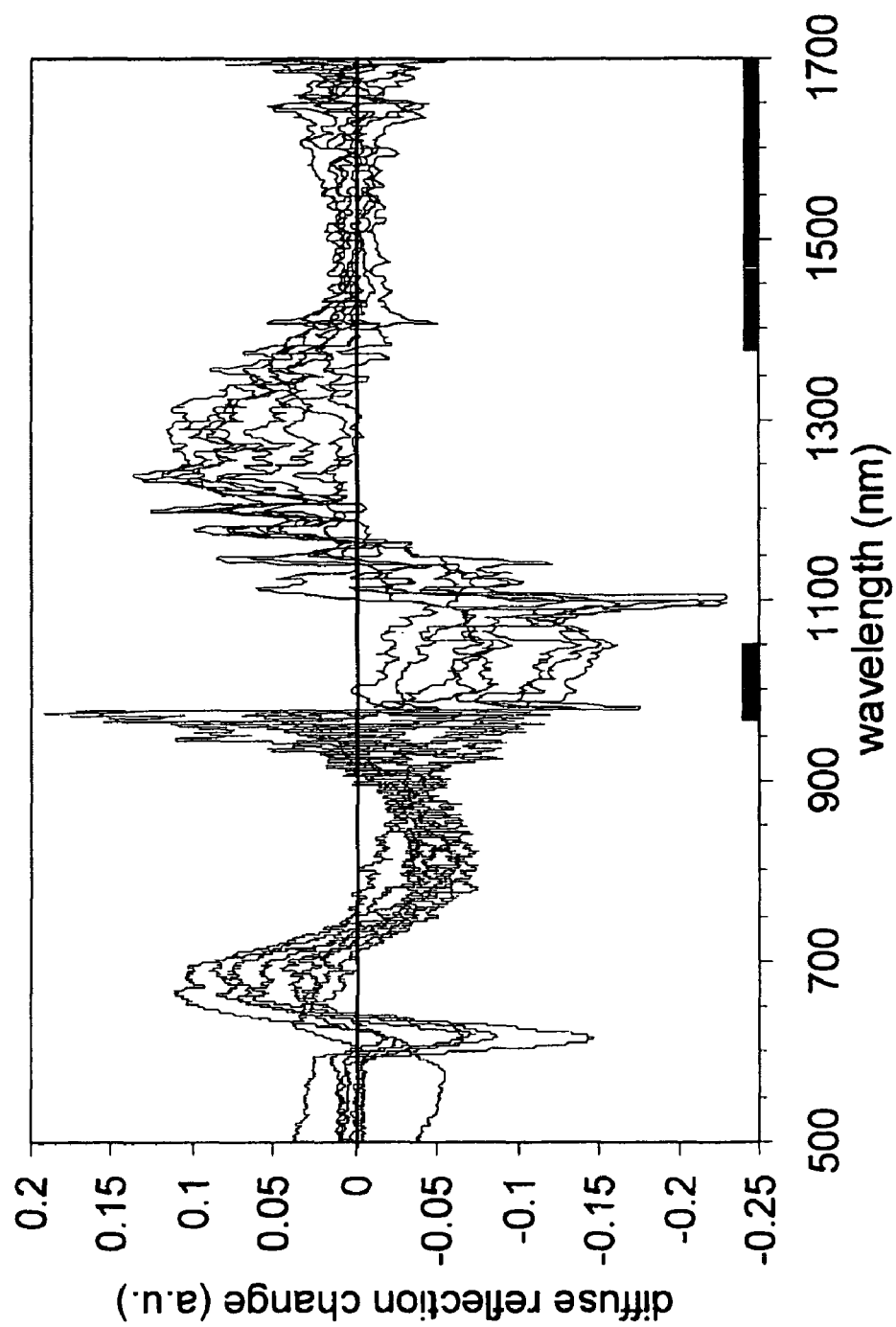

An optical difference spectrum (post-treatment—pre-treatment) was derived from the data shown in FIG. 1 for each patient and measurement mode and is given in FIG. 2. In the difference spectra coinciding local extrema were observed as well as isobestic wavelengths of near-zero change for all patients, which differ in location depending on the light interaction mode. Interestingly (and not obvious from the monochrome plot), was the difference observed between patients in both the magnitude of change across the spectrum and among the two modes. For example, for first three local extrema in transmission (FIG. 2*a*), Patient 6 exhibited the largest change while Patient 4 exhibited the largest change for the following two extrema. In diffuse reflection (FIG. 2*b*) however, Patient 2 showed the largest change at the first minimum while Patient 3 showed the largest change at the following peak and Patient 4 showed the largest change at the next minimum.

Possible origins of the complex spectral changes observed include an alteration in the concentration, binding or other molecular properties of hemoglobin or changes in the environment surrounding hemoglobin, as well as possible changes in water constitution including electrolyte levels, acidity, and intra/extra-cellular fluid balance and hydration[19, 20].

Periodic fluctuations observed in the diffuse reflection change at longer wavelengths are due to multiple reflections caused by the blood, optical cell, and air interfaces. Also, transmission spectra exhibit greater signal-to-noise ratio than the diffuse reflection spectra due to the higher absolute optical power levels detected in transmission. As described earlier, only a portion of the diffusely reflected light (20° solid angle) was captured in the present setup resulting in a lower absolute intensity level. It has been reported that increasing the solid angle of collection of diffusely reflected light using an integrating sphere significantly improves the quality of whole blood spectra[21].

3.3. Correlation with Clinical Measures

To confirm that the observed whole blood spectral changes were consistent with clinical parameters used in routine patient care, changes in clinically-based measures of hemodialysis were correlated with the difference spectra. For each patient, clinical charts were used to compile key measures of hemodialysis performance to allow a direct comparison of optical measurements and clinical outcomes. The analysis presented here focuses on a few key clinical measures of hemodialysis treatment: the urea reduction ratio (URR=1−post/pre blood urea concentration); a derived measure, the potassium reduction ratio (KRR=1−post/pre blood potassium ion concentration); a derived measure relating to fluid removal by filtration, the weight retention ratio (WRR=post/pre body weight); and Kt/V (dialysis dose, where K is urea clearance rate of the dialyzer in L/min, t is treatment time in min and V is the urea distribution volume for the patient in L).

The clinical values for the chosen measures along with the range of values among the patient group are shown in Table 2. The value of Pearson's correlation coefficient r among the clinical parameters has also been given in Table 2. A nearly perfect positive correlation was found between URR and Kt/V which was expected given that Kt/V values are derived from the URR of a patient[22]. URR thus suffices to describe the behavior of Kt/V in the following analysis. Furthermore, while absolute potassium reduction is used as an accepted clinical measure, KRR was derived for the purposes of this study to provide a relative, unit-less parameter for consistency in the analysis. Absolute potassium reduction and the KRR were highly correlated ($r > 0.97$) indicating nearly identical behavior.

TABLE 2

Hemodialysis parameter values for the patient group obtained from clinical blood laboratory results and patient charts. Minimum and maximum parameter values within the group are also given. Correlations among the parameter values are also shown.

| | Hemodialysis Measure | | | |
|---|---|---|---|---|
| Patient | WRR | URR | KRR | Kt/V |
| 1 | 0.975 | 0.755 | 0.261 | 1.80 |
| 2 | 0.945 | 0.768 | 0.318 | 1.88 |
| 3 | 0.970 | 0.765 | 0.220 | 1.88 |
| 4 | 0.958 | 0.855 | 0.453 | 2.24 |
| 5 | 0.960 | 0.775 | 0.396 | 1.88 |
| 6 | 0.946 | 0.830 | 0.395 | 2.12 |
| 7 | 0.979 | 0.791 | 0.217 | 1.96 |
| 8 | 0.953 | 0.728 | 0.415 | 1.72 |

| | Weight | Urea | Potassium |
|---|---|---|---|
| Min value | 62 kg | 2.7 mM | 2.6 mM |
| Max value | 100 kg | 27.2 mM | 5.3 mM |

| | Parameter Correlation | | | |
|---|---|---|---|---|
| | WRR | URR | KRR | Kt/V |
| WRR | — | −0.171 | −0.704 | −0.190 |
| URR | | — | 0.369 | 0.997 |
| KRR | | | — | 0.370 |
| Kt/V | | | | — |

Additionally in Table 2 correlations were observed between WRR and KRR as well as URR and KRR. To remove the effect of intervening parameters, the partial correlation coefficient $r_{xy,z}$ has been used to represent the correlation of x (the set of optical difference values at a given wavelength data point in FIG. 2) with y (the set of clinical parameter values), while removing the influence of z (a correlated clinical parameter). The result is a partial correlation spectrum for each clinical parameter in both transmission and diffuse reflection modes with the influence of the clinical parameter with the highest correlation with the chosen parameter partialed out. Using the two-tailed t-test for significance of the partial correlation statistic with N=8 patients yields critical values of $|r|=0.754$ and 0.874 to be significant at the $P=0.05$ and 0.01 levels, respectively. The partial correlation spectra for the WRR, URR, and KRR are given in FIG. 3. Correlation spectra from a single optical interaction mode (transmission or diffuse reflection) have been shown for each parameter as the other mode did not exhibit regions of correlation exceeding the P=0.05 critical value. Analysis of the correlation spectra has been restricted to wavelength regions with adequate signal-to-noise ratio and where the correlation coefficient exceeded the critical value over a broad wavelength range (>5 nm). Sharp, noise-like spikes in the correlation coefficient have thereby been excluded from the analysis. Wavelength regions of significant correlation with clinical parameters are summarized in Table 3.

TABLE 3

Figure 3A:
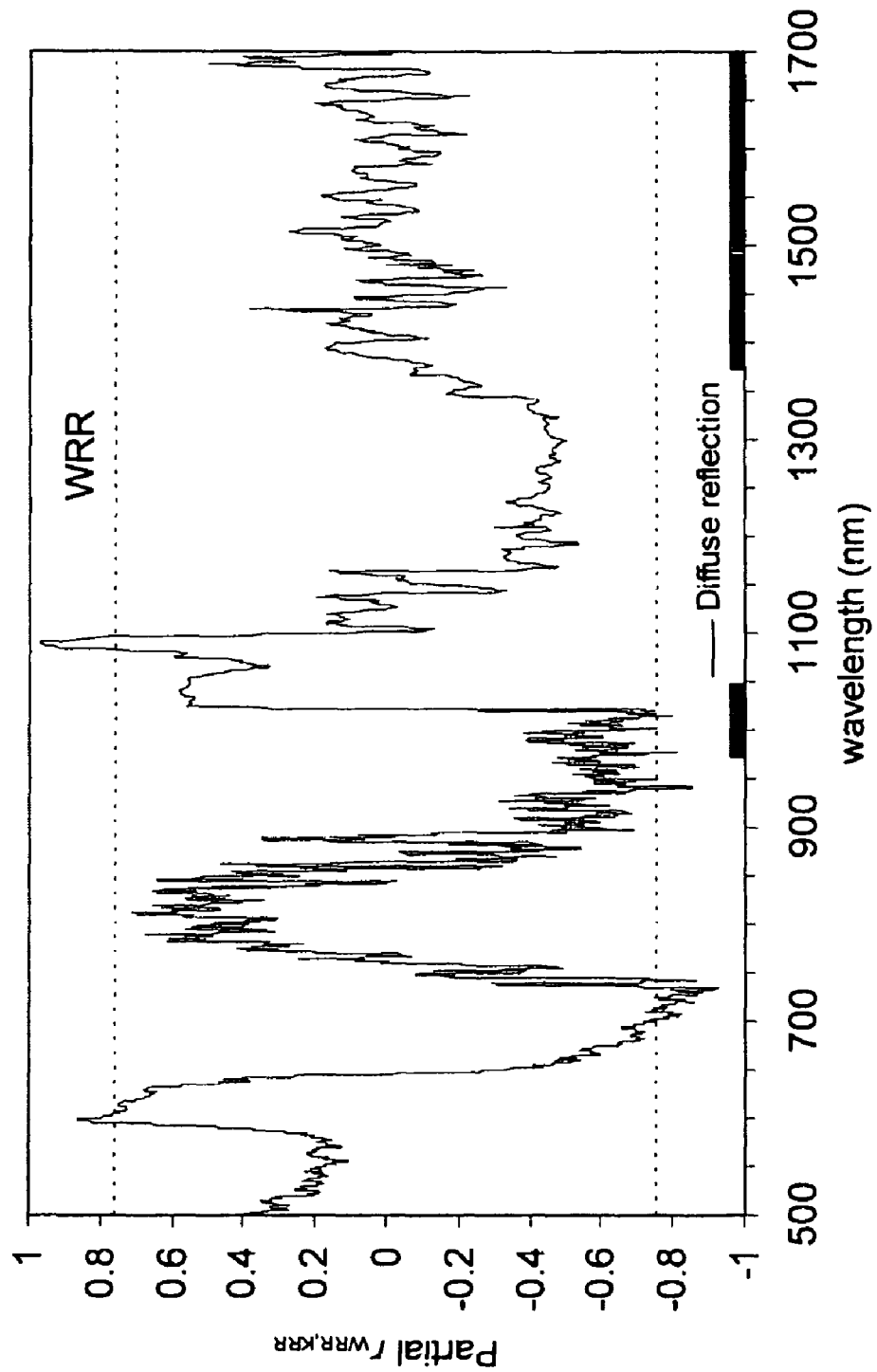
FIG. 3: Partial correlation spectra for (a) WRR with the effect of KRR removed, (b) URR with the effect of KRR removed and (c) KRR with the effect of WRR removed. The spectra represent partial correlation with the measured transmission or diffuse reflection difference spectra from FIG. 2. Horizontal lines indicate $r_{crit}$ for significance at the P=0.05 level, while shaded regions indicated on the abscissa have been excluded from the analysis due to low signal-to-noise ratio.
Figure 3B:
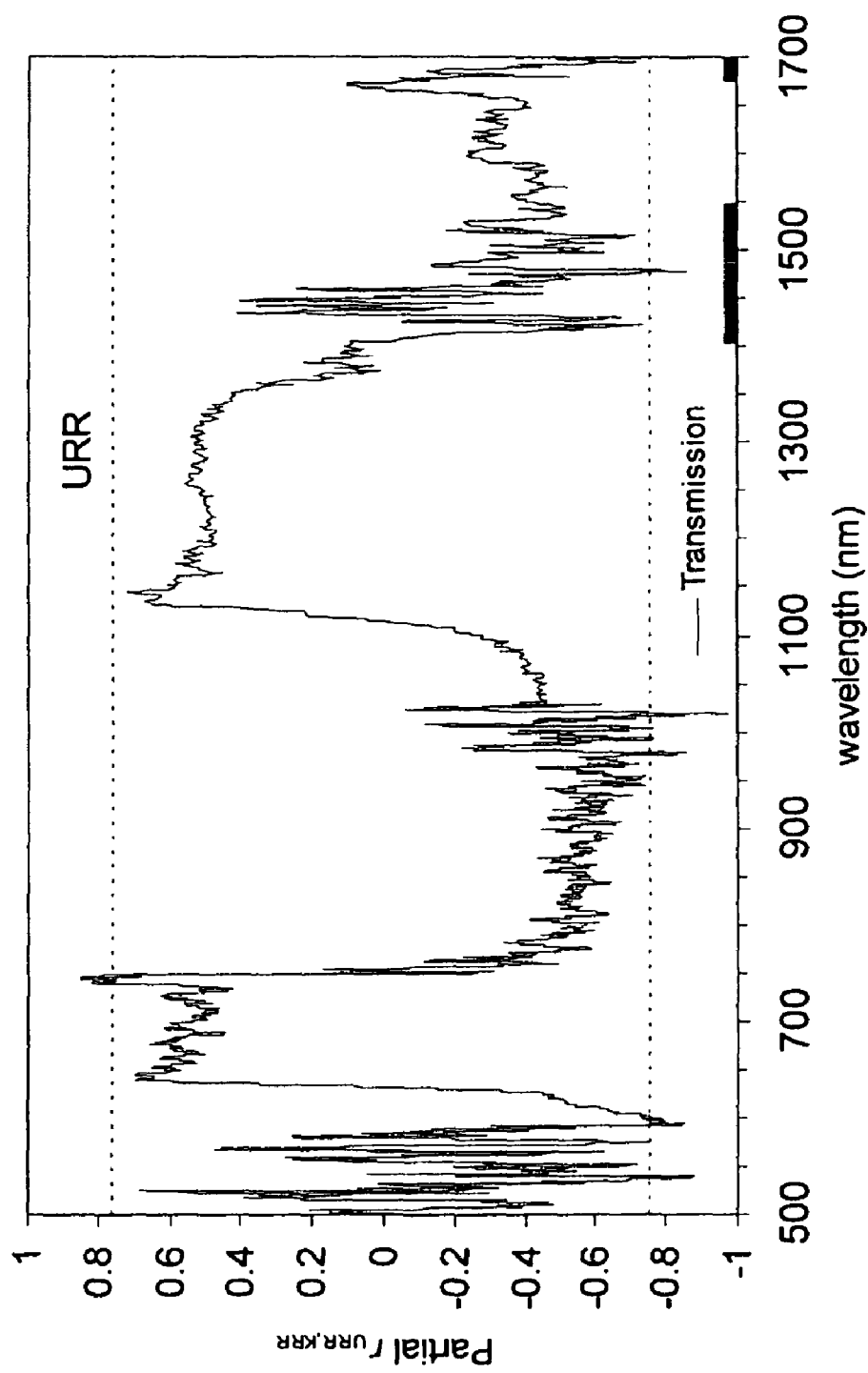
Figure 3C:
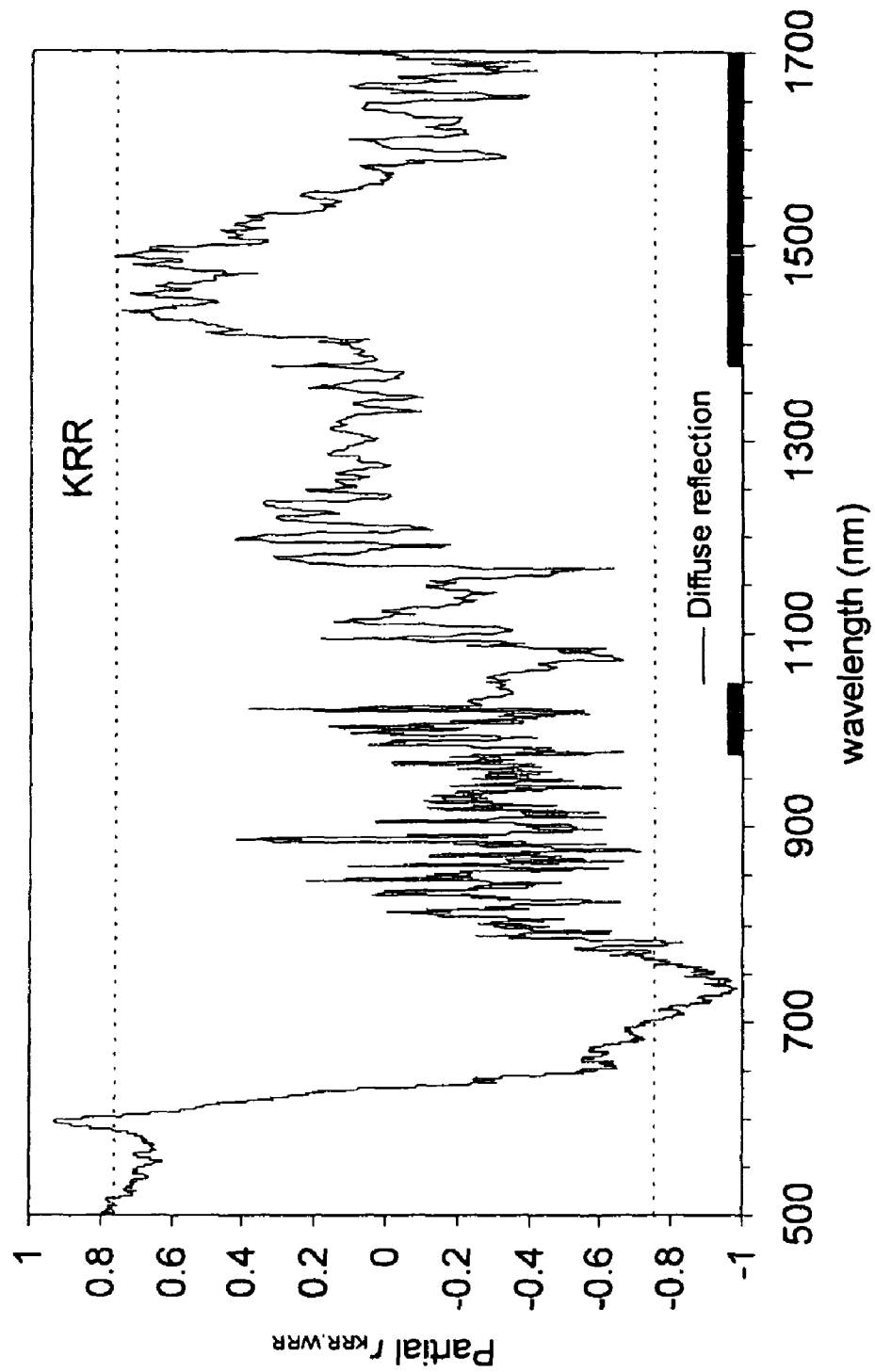

Wavelength regions of clinical parameter correlation r exceeding the critical value $r_{crit}$ for significance at the P = 0.05 level over a wavelength band >5 nm as determined from FIG. 3. Within each region the peak correlation coefficient value $r_{max}$ is given along with the corresponding two-tailed significance level (P-value) for $|r| > |r_{max}|$.

| Clinical Parameter | Wavelength range (nm) $|r| > r_{crit}$ | Peak correlation coefficient $r_{max}$ | Significance (P-value) $|r| > |r_{max}|$ |
|---|---|---|---|
| WRR | 595-605 | 0.869 | 0.011 |
|  | 702-710 | −0.824 | 0.023 |
|  | 716-735 | −0.931 | 0.002 |
|  | 1085-1094 | 0.972 | 0.0002 |
| URR | 593-599 | −0.851 | 0.015 |
|  | 740-748 | 0.854 | 0.014 |
| KRR | 588-602 | 0.933 | 0.002 |
|  | 702-764 | −0.984 | <0.0001 |

Several wavelength regions of diffuse reflection change (centered at 600 nm, 720 nm, and 1090 nm) were highly correlated to the WRR. Correlations below 1000 nm are likely to represent a modification in the scattering environment of the hemoglobin molecule or red blood cells (RBCs) caused by either the direct removal of fluid (source of the weight change) or the removal of analytes along with the fluid that may influence hemoglobin. The strongest observed correlation was above 1000 nm where water absorption dominates the spectrum, possibly indicating the relation between fluid removal through hemodialysis and a change in water content of the blood.

Regions of significant URR correlation with optical transmission change were observed centered at 595 nm and 745 nm. It has been suggested that the correlation with optical transmission in the 595 nm region is related to urea-mediated blood cell volume changes[19]. In addition, second- and third-order overtones of the N-H symmetric and asymmetric stretching vibrations in the urea molecule are broad bands centered at 960-1000 nm and 720-750 nm, respectively[6]. First order overtones of these stretches occur in the 1450-1500 nm region, but these are buried under the strong water absorption band in this region[6]. The observed correlation around 745 nm corresponds well to the third-order N-H overtone while high correlations in the second-order overtone region were also observed (as seen in FIG. 3) but did not exceed the critical value for significance over a 5 nm window and have therefore been excluded from Table 3.

Significant correlation for the KRR was observed in two broad regions. Accordingly, potassium ions in whole blood have been shown to exhibit a broad correlation in the 500-1000 nm wavelength region[20]. The observed regions of high correlation may correspond to the ion concentration itself or to the indirect effects of its removal. The latter effect is plausible as the potassium ion balance between intracellular and extra-cellular fluid can influence blood cell volume thereby affecting the scattering of light.

4. Discussion

To our knowledge, the present study documents for the first time the change in the optical transmission and diffuse reflection spectrum of whole blood resulting from a hemodialysis treatment session. Using visible and near infrared wavelengths, a statistically significant whole-spectrum change due to treatment was found for both light interaction modes. The clear distinction of pre- and post-dialysis blood in this manner can serve as the basis for a useful approach to on-line hemodialysis monitoring. When calibrated with a larger spectral database from multiple treatments, an online measure such as the principal component score could be used to monitor the progress of a treatment session. As the score reflects multiple blood parameters including unfiltered analytes, it can provide a means to determine the adequacy of treatment and can be a candidate for a comprehensive indicator of longer-term clinical patient outcomes.

Although the patients recruited in this study represented a cross-section of age, gender, and clinical condition, the observed spectral shape changes due to treatment were consistent among patients, though the magnitude of change differed substantially.

In this study a few key clinical measures of uremic toxicity and hemodialysis adequacy were chosen and shown to correlate with whole blood optical transmission and diffuse reflection change in certain spectral bands. The spectral bands of high correlation had in most instances a plausible explanation due to molecular or clinical factors, a result which serves to validate the spectroscopy methods employed. Upon comparison of FIGS. 2 and 3, however, it is evident that broad regions of optical change due to hemodialysis do not necessarily correspond to similar regions of high correlation for the chosen clinical measures. Instead, direct changes in urea and potassium may only have minor effects on the optical spectrum compared to their indirect effects in altering the optical properties of blood. The bulk of the optical property changes seen were likely due to changes in the molecular and cellular environment of major absorbing and scattering components in whole blood, namely hemoglobin, oxygen, water, and red blood cells (RBCs). Besides the chosen clinical measures, a host of other factors and processes could potentially modify this environment. To exemplify this point, clinical observations indicate that prior to hemodialysis treatment patients usually exhibit a mild metabolic acidosis, while the effect of bicarbonate in standard dialysate solution results in a mild alkalosis post-treatment[23]. Using near infrared spectroscopy of whole blood it has been reported that pH-induced changes in the hemoglobin molecule correlate with RBC size and oxygen saturation changes[24,25]. Such changes would directly modify the optical absorption and scatter properties of whole blood. An additional related factor is sodium, which plays an important role in fluid balance regulation and directly affects the RBC volume, strongly influencing optical absorption and scatter in the near infrared region[10]. In addition, urea removal has also been proposed as a contributor to RBC volume change[19]. Moreover, in addition to the amplitude changes observed in FIG. 2, directional changes of extrema are also evident, where minima for some patients correspond to maxima for others. This indicates possible competing processes and patient-specific responses, further illustrating the complex nature of hemodialysis-induced changes in whole blood. The broad spectral effects observed are not easily accounted for by measuring the concentration of a few analytes. While certain correlations between optical properties in blood and clinical parameter levels exist, the relation is unlikely a simple causal one. In this respect, full optical spectrum measures can be more useful in assessing broader factors such as disease status, treatment efficacy, or patient outcomes.

Correlation between measured spectra and the clinical indicators chosen may also be affected by the use of serum-based analyte levels in the clinic. While analyte levels in hemolyzed blood may better correlate with whole-blood spectral changes, routine laboratory analysis procedures were followed in the study as these represented the clinical standard upon which patients were assessed and treatment was routinely delivered.

A potential confounding factor in this study was the chance that oxygen saturation ($O_2$-sat) changes in blood could significantly influence optical properties primarily below 1100 nm. In the present study mixed arterio-venous blood was drawn following standard clinical protocol. Blood drawn in this manner typically has a high partial pressure of oxygen and a corresponding high $O_2$-sat, as confirmed by the similarity and consistency of measured pre- and post-dialysis spectra with that of pure oxyhemoglobin as seen in FIG. 1c. The maintenance of $O_2$-sat levels during hemodialysis has also been noted by others[10]. Spectral features characteristic of a change in the high $O_2$-sat level are also absent from the measured difference spectra. In particular, spectral shape changes in the 540-580 nm double-peak region and changes in the 760 nm region due to the presence of deoxyhemoglobin[16] are absent in the difference spectra shown in FIG. 2. These factors indicate that $O_2$-sat changes were minimal and therefore had a negligible confounding effect upon the analysis.

Another potential confounder in the analysis was the change in hematocrit level due to treatment. As hemodialysis removes fluid while the blood cells remain, a hemoconcentrating effect is expected leading to an increased fraction of optically absorbing and scattering species within the blood. Because the standard clinical protocol used in this study excluded post-dialysis hematocrit determination, the influence of hematocrit was investigated using a separate set of blood samples from ten hemodialysis patients. Hematocrit change due to treatment was determined by volumetric hematocrit determination after centrifuging, followed by comparison of pre- to post-dialysis levels. Change in hematocrit was subsequently compared to the transmission and diffuse reflection spectrum changes measured in the samples. Hematocrit change due to treatment was found to vary from −17% to +20%, reflecting both an increase due to hemoconcentration as well as a counteracting effect due to rapid plasma refilling in some patients. Hematocrit changes were compared with transmission and diffuse reflection changes in the samples and no significant correlation was found in the 500-1700 nm wavelength range (data not shown). The effect of hematocrit change on the observed spectral changes is therefore expected to be minimal.

Although in this study no attempt was made to smooth, filter, or pre-process the spectral data, such schemes can be useful in extracting meaningful spectral information for molecular identification[2,7,21] or disease pattern recognition[11]. With a larger patient group and a broader set of clinical parameters, multivariate methods such as PCA, linear discriminant analysis, and the partial least squares method can be used with the full optical spectrum to investigate the underlying mechanisms resulting in the observed blood changes and to potentially predict treatment outcomes.

Finally, although measurements in the present study were limited to wavelengths shorter than 1700 nm, it is beneficial to use the entire near infrared wavelength range (up to 2500 nm). Fundamental overtones of molecular vibrations present at longer wavelengths yield more distinct spectral features and thereby a more robust characterization of whole blood properties. While the absorption due to water increases at longer wavelengths, useful features in whole blood spectra throughout the near infrared region have been reported in the literature despite this interference[26,27].

5. Conclusion

In the present study, changes in whole blood resulting from hemodialysis treatment for ESRD were investigated using transmission and diffuse reflection spectroscopy in the 500-1700 nm wavelength region. Using the PCA method, the full optical spectrum of blood from 8 patients was analyzed and it was found that a significant difference could be detected between dialyzed versus undialyzed blood in the patient group at a level of $P<0.01$ in both transmission and diffuse reflection modes. Consistent changes in transmission and diffuse reflection difference spectra were also observed among the diverse patient group as a result of treatment. The difference spectra were shown in certain wavelength regions to have significant correlation with clinical measures of hemodialysis including fluid removal, urea, and potassium (P 0.01 for all measures). While the spectroscopic techniques presented may provide a limited usefulness in monitoring specific molecular parameters, the complexity of hemodialysis-induced changes in whole blood indicate a full-spectrum monitoring approach can be better suited to the investigation of macroscopic clinical questions relating to hemodialysis adequacy, disease progression, and overall toxicity. Wide-spectrum monitoring combined with a database of spectral patterns can enable complex relations among numerous parameters to be recognized as a pattern differing from an ideal or baseline. In this manner an ensemble of physiologic and molecular changes in the blood are monitored together with an implicit weighting. The resulting patterns may correlate better with treatment-related complications, disease progression, and quality-of-life factors than current clinical parameters. With rapid, non-contact and non-destructive monitoring, both time- and wavelength-resolved information could be significantly more useful, and it is apparent that extending the present technique to an online system would be valuable to investigating the provision of optimum hemodialysis for the ESRD patient population.

Example 2

Correlation of Spectral Data to Clinically Relevant Parameters

Whole-blood samples from 3 hemodialysis (HD) patients were extracted before a typical HD session, every hour during the treatment, and after the session. In total, each patient was sampled five times with one hour between samples (4-hour HD session). Each hour, two blood samples were taken from each patient; one was sent to a laboratory for standard blood analysis and the other was subjected to analysis with a spectrophotometer. The transmission and diffuse reflection spectra of each whole blood sample was taken using the methodology and instrumentation as described in Example 1, although one skilled in the art could obtain such spectra by a number of methods and using various instrumentation.

The blood laboratory quantified levels of the following clinical parameters in the blood samples: hemoglobin, hematocrit, potassium, carbon dioxide, urea, creatinine, phosphate, using standard clinical chemistry techniques and analyzers.

Additionally, oxygen saturation ($O_2$-sat) was quantified from the samples analyzed in the spectrophotometer.

The $O_2$-sat value for each blood sample was estimated using the whole-blood spectrum, similar to the method employed in clinical oximeters, Each mean blood spectrum was fitted to a linear combination of published absorption spectra of pure oxyhemoglobin and deoxyhemoglobin in the 600-950 nut spectral region. Each fit was optimized by varying both the oxyhemoglobin to total hemoglobin (oxyhemoglobin+deoxyhemoglobin) ratio ($O_2$-sat) and a linear offset value in order to maximize the coefficient of determination ($R^2$) between the measured spectrum and the fit. The fit was performed using the built-in Excel solver (Excel 2002; Microsoft, Inc., Redmond, Wash.) and yielded optimum $O_2$-sat estimates for each sample.

Figure 4A:
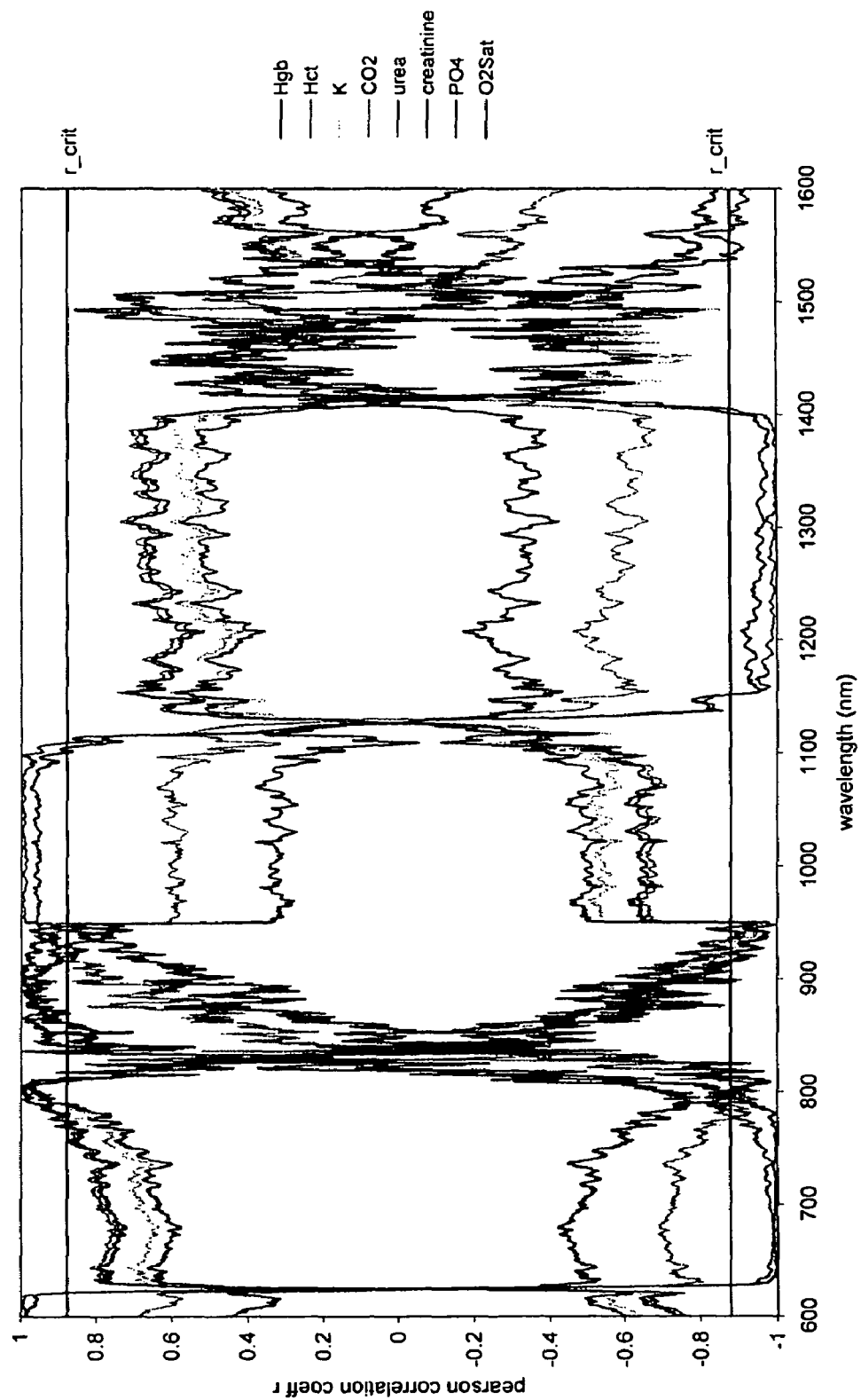
FIG. 4: Correlation spectra obtained from a hemodialysis patient; A Transmission spectra and B Diffuse Reflection spectra.
Figure 4B:
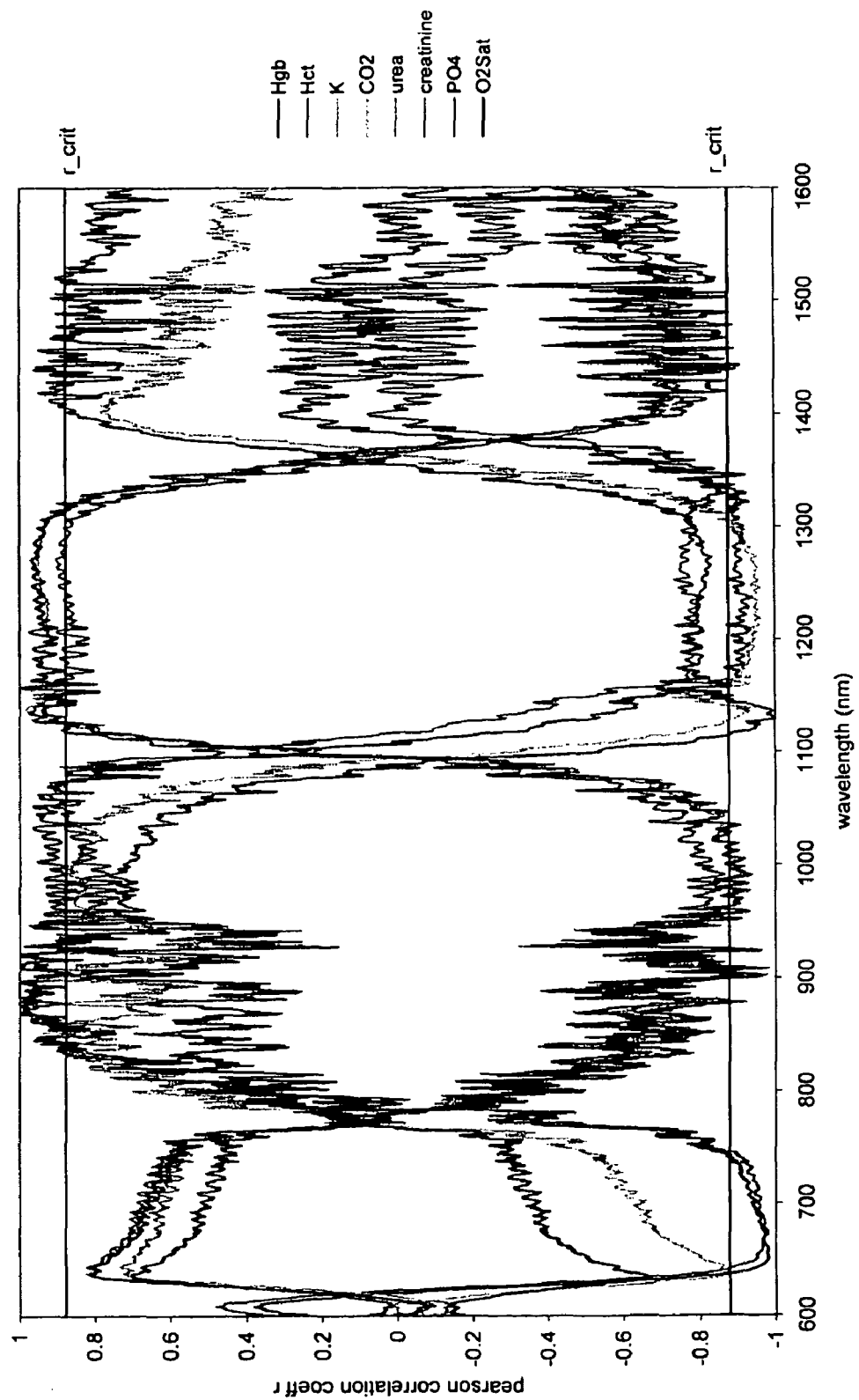

Transmission and diffuse reflection from the five blood samples from a typical patient were measured in the wavelength region spanning 600 nm to 1600 nm. The spectra were area-normalized, mean-centered, and plotted in absorbance units (as described in Example 1). At each wavelength data point, the five absorbance values were correlated with values of each laboratory-measured blood parameter, using Pearson's r. The resulting correlation spectra are shown in FIG. 4.

In addition, the Pearson correlation was repeated amongst the clinical variables themselves, to yield the following result:

|  | Hct | K | $CO_2$ | urea | Creatinine | $PO_4$ | $O_2$Sat |
|---|---|---|---|---|---|---|---|
| Hgb | 0.962 | −0.745 | 0.790 | −0.833 | −0.816 | −0.689 | 0.554 |
| Hct |  | −0.541 | 0.604 | −0.654 | −0.630 | −0.472 | 0.307 |
| K |  |  | −0.940 | 0.978 | 0.982 | 0.979 | −0.952 |
| $CO_2$ |  |  |  | −0.947 | −0.949 | −0.907 | 0.896 |
| Urea |  |  |  |  | 1.000 | 0.974 | −0.920 |
| creatinine |  |  |  |  |  | 0.980 | −0.931 |
| $PO_4$ |  |  |  |  |  |  | −0.977 |

For these results, the critical level for two-tailed significance of r is $r_{crit}$=0.878 at the 95% confidence level. Highlighted values in the above table indicate significant correlation among clinical parameters.

There are two groups of correlated clinical variables, and they are mutually exclusive (i.e., uncorrelated with each other):

Group 1: hemoglobin, hematocrit;

Group 2: potassium, urea, carbon dioxide, creatinine, phosphate, oxygen saturation Looking at the correlation plots in FIG. 4, significant correlation of Groups 1 and/or 2 were noted in various spectral regions. In transmission, hemoglobin/hematocrit correlates highly with most of the spectrum below 1400 nm, while in diffuse reflection, this correlation was weaker. Hemoglobin/hematocrit is expected to correlate with transmission as the optical absorption of hemoglobin dominates whole blood by at least two orders of magnitude.

If Group 1 is considered as a source of interference, then spectral regions in both transmission and diffuse reflection were identified where Group 2 has high correlation and Group 1 has low correlation (i.e., transmission: 800-820 nm, 940-960 nm; diffuse reflection: 1130-1320 nm). These are potential regions for monitoring patient toxicity over time, in particular for the patient studied herein. Each patient may have a slightly different spectral region for monitoring toxicity.

The present example serves to illustrate one method for using two different light-tissue interaction techniques to extract potentially clinically-relevant information from the optical spectral data.

Example 3

Correlation Method Using an Aggregate Spectrum

Another approach to incorporate more than one technique to extract clinically-relevant information from optical spectra is to concatenate the spectra from two techniques together to create an 'aggregate spectrum'. This aggregate spectrum represents two distinct types of information (i.e., cell properties and properties of the extracellular space, or electronic and vibrational molecular states of molecules in the tissue, etc.). Information contained within multiple aggregate spectra can be used with established data reduction techniques, such as singular value decomposition, partial least squares or principal component analysis, to extract indices of high correlation with an observed clinical condition, its progression or its treatment.

Blood samples were taken from 10 HD patients and 10 healthy control subjects as described below.

Blood samples were collected from end-stage renal disease (ESRD) patients and from healthy subjects. All subjects gave voluntary consent and the study protocol and use of human subjects was approved by the Ottawa Hospital Research Ethics Board. ESRD patients were chosen from the patient population undergoing 3× weekly chronic hemodialysis treatments at the Ottawa Hospital (General Campus) Dialysis Unit. Patients with active infections were excluded from the study: no other exclusion criteria were used. Vascular access was via an arterio-venous fistula or tunneled central venous catheter. Prior to the initiation of hemodialysis, patients received a standard dose of heparin to minimize the risk of coagulation during treatment.

In addition to the measurement of the diffuse reflection spectrum from these whole blood samples, the transmission spectrum was also taken (as described in Example 1).

A principal component analysis was performed using the diffuse reflection spectra alone, the transmission spectra alone, and the combined diffuse reflection and transmission spectra. The table below indicates the results of the analysis:

|  | Transmission only | | Diffuse reflection only | | Combined | |
| --- | --- | --- | --- | --- | --- | --- |
| Principal Component | Eigen value | % explained variance | Eigen value | % explained variance | Eigen value | % explained variance |
| 6 | 0.0262 | 0.64 | 0.0135 | 0.52 | 0.0889 | 0.71 |
| 5 | 0.0619 | 1.51 | 0.0232 | 0.9 | 0.1048 | 0.83 |
| 4 | 0.0726 | 1.77 | 0.0365 | 1.41 | 0.3693 | 2.93 |
| 3 | 0.1983 | 4.84 | 0.2925 | 11.3 | 0.5546 | 4.41 |
| 2 | 0.7777 | 18.98 | 0.603 | 23.3 | 1.9178 | 15.24 |
| 1 | 2.9179 | 71.23 | 1.6001 | 61.84 | 9.3855 | 74.57 |
| Total % | | 98.97 | | 99.27 | | 98.69 |

The eigenvalues from the three analyses are different as are the distributions of level of explained variance among the eigenvalues, indicating differences in the information content of the analysis when both techniques are used together. The principal component scores for each blood sample with respect to the first six principal components are also different for each analysis. The combined analysis, taking into account a larger data set, produces a set of indices (the principal component scores) that are fundamentally different from indices created using a single data set (technique) alone. Indices thus derived from the combined analysis can correlate better with an observed clinical condition, progression of a condition or its treatment, than would indices derived from a single analysis alone.

Example 4

Use of Principal Component Plots

A set of whole blood samples was obtained from 13 HD patients pre and post-dialysis in a similar manner as the samples were obtained in previous examples. Transmission spectra were obtained as described in Example 1. Additionally, the global mean of each spectrum was removed from that spectrum (offset removal), and a principal component analysis (PCA) was performed on this mean-shifted data. Note that the first step in the PCA algorithm is to subtract from each data point the mean of all absorbance values at that wavelength (mean subtraction).

From the PCA, the proportion (in percent) explained variance from each principal component is given below for the first 6 principal components (PCs), which together accounted for 99.1% of the variance in the data set.

| Principal Component | Explained variance (%) |
| --- | --- |
| 6 | 0.48 |
| 5 | 2.6 |
| 4 | 4.55 |
| 3 | 9.52 |
| 2 | 21.32 |
| 1 | 60.63 |

Figure 5:
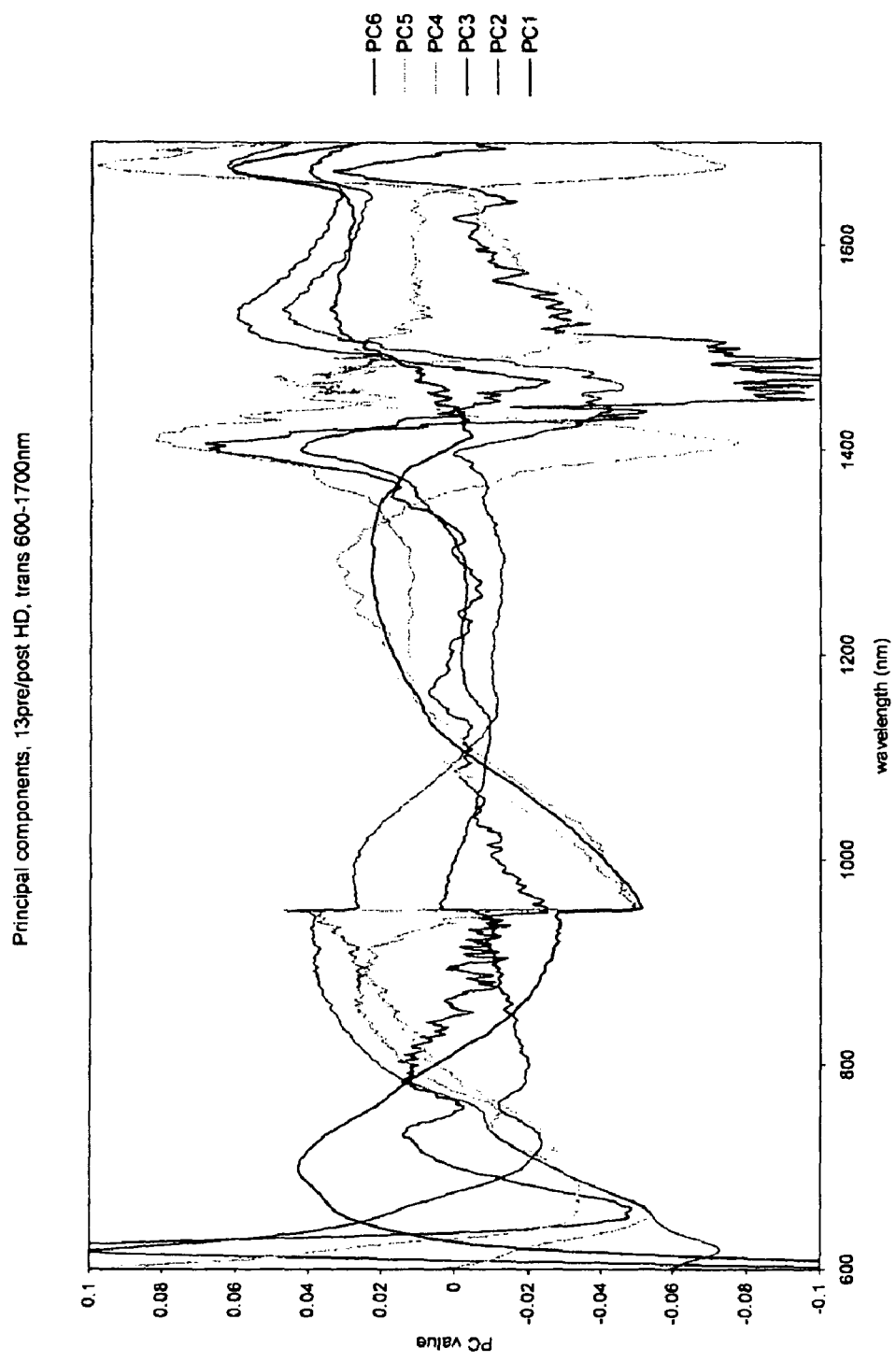
FIG. 5: A plot of principal components (eigenvectors) for 13 patients pre- and post-hemodialysis.

The principal components themselves (eigenvectors) are plotted in FIG. 5.

Figure 6A:
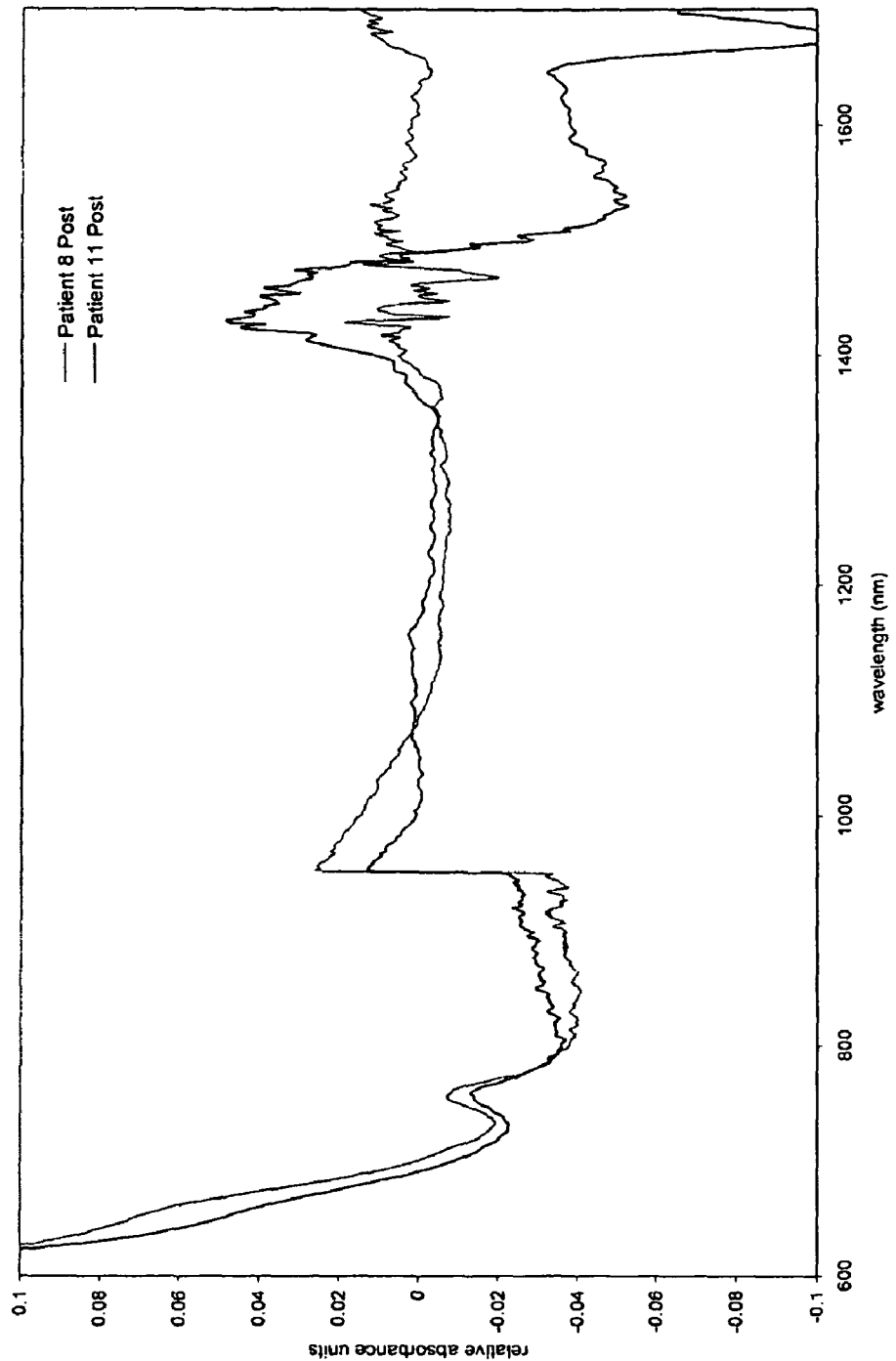
FIG. 6A depicts transmission spectra of typically low oxygenated samples, mean subtracted
Figure 6B:
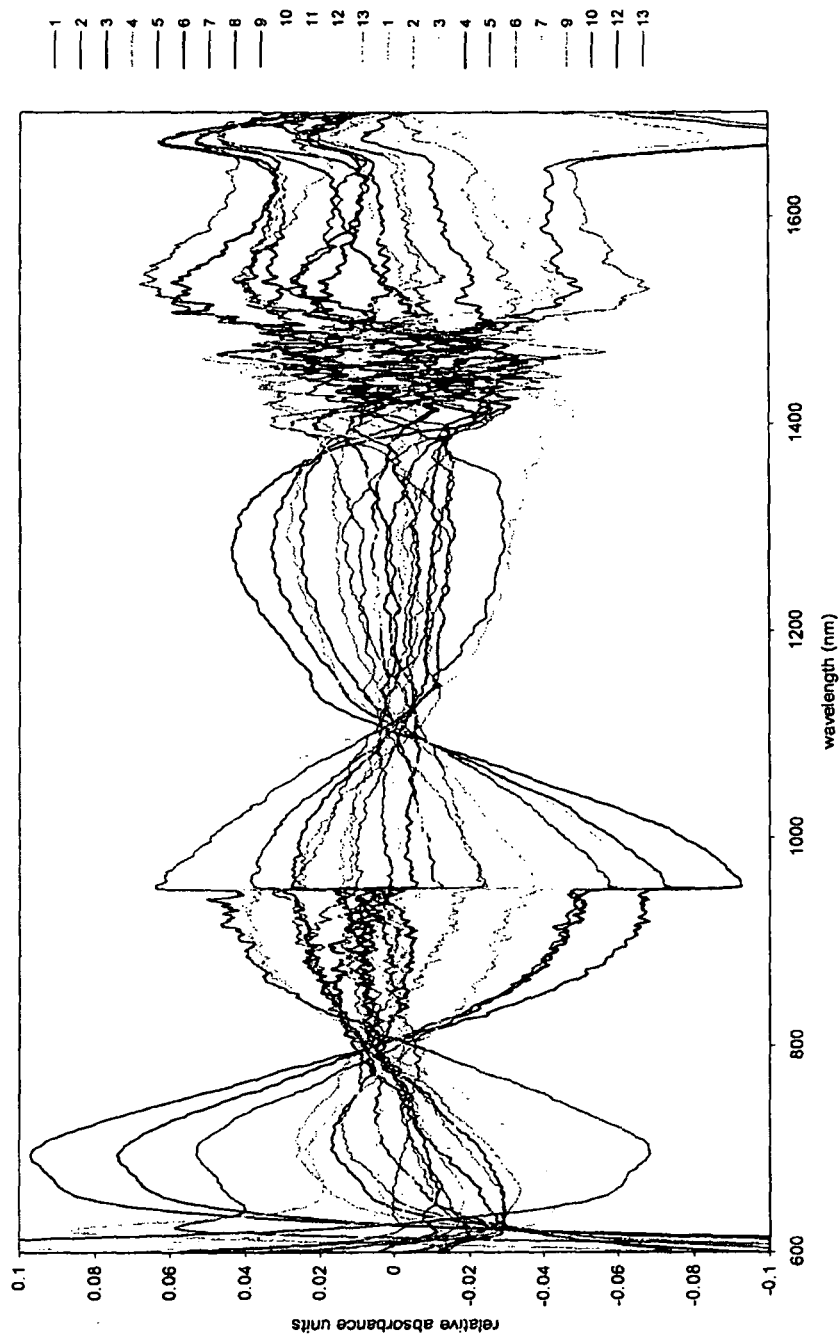
FIG. 6B depicts transmission spectra of typically high oxygenated samples, mean subtracted.

Oxygen saturation (a potential source of interference) was assessed in each of the 26 blood samples by the technique described in Example 2, which uses a different light-tissue interaction method (diffuse reflection). Two of the 26 spectra had a lower oxygen saturation (<97%). These two spectra (in mean-subtracted form) are shown in FIG. 6A, while the rest are shown in FIG. 6B.

Figure 7:
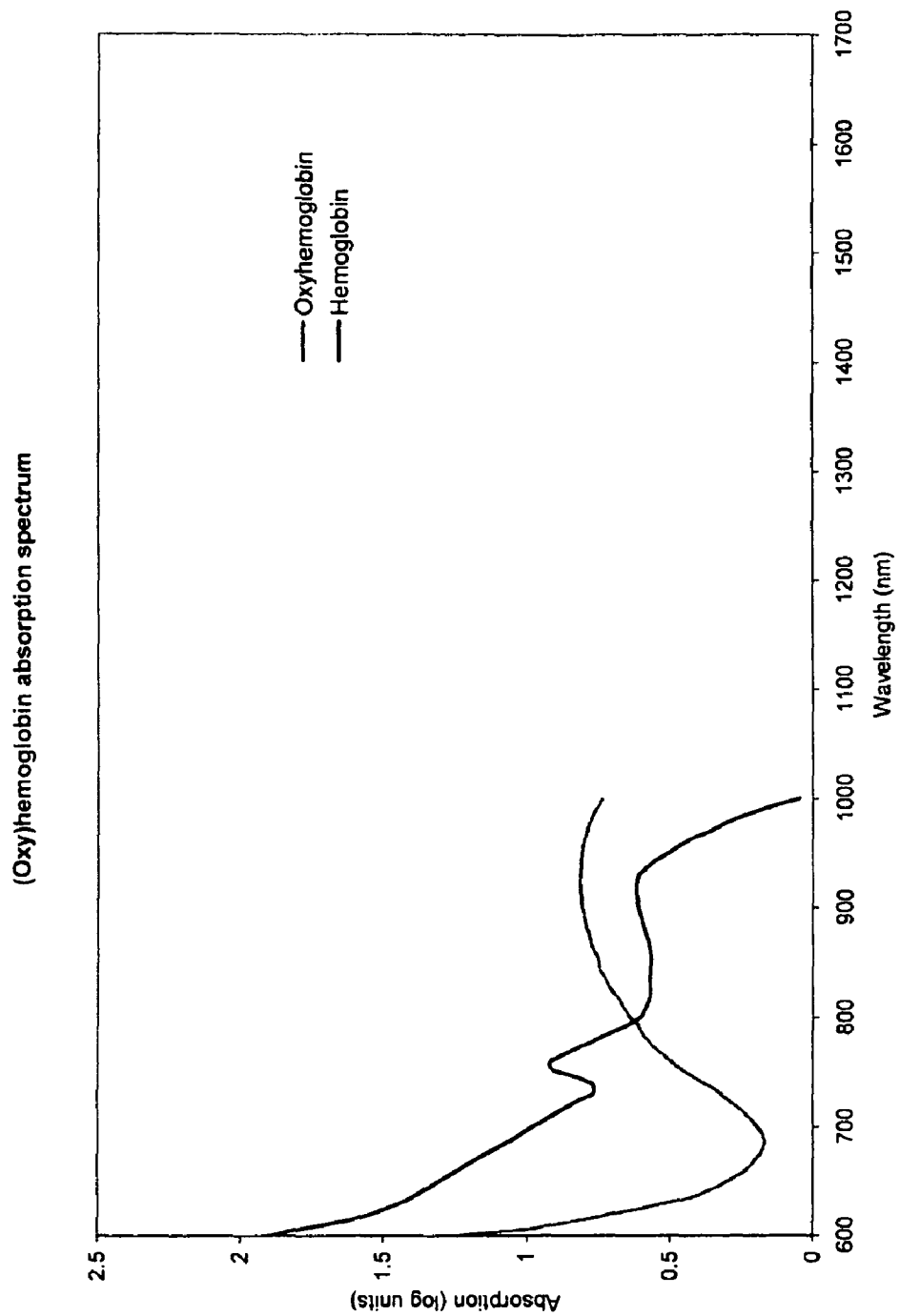
FIG. 7 depicts known oxyhemoglobin and deoxyhemoglobin spectra.

For reference, the published oxyhemoglobin and deoxyhemoglobin spectra are given in FIG. 7 (taken from S. Prahl, "Optical absorption of hemoglobin," http://omlc.ogi.edu/spectra/hemoglobin/.).

Comparing this to the PC plot, PCs 2, 3, 4, 6 all have the 740 nm deoxyhemoglobin peak. PC3 in particular is very similar to the deoxyhemoglobin spectrum in the 600-950 nm region. PCs 1 and 5 do not seem to be affected by oxygenation.

A pearson correlation was performed with the estimated oxygen saturation level, the measured hematocrit level in the samples and the first 6 PCs:

|  | PC6 | 5 | 4 | 3 | 2 | 1 |
| --- | --- | --- | --- | --- | --- | --- |
| O$_2$Sat | −0.088 | 0.054 | 0.185 | −0.735 | 0.634 | −0.183 |
| Hct | −0.258 | 0.424 | −0.437 | −0.252− | 0.203 | −0.361 |

PCs 2 and 3 are significantly correlated with oxygenation (based on a two-tailed significance threshold $r_{crit}$=0.561 for significance at the 99% level). The only PCs that do not resemble the deoxyhemoglobin spectrum are PC1 and PC5.

PC1 and PC5 could therefore be considered 'indices' for the hemodialysis treatment, substantially free from interference due to oxygen saturation in the blood sample.

Figure 8:
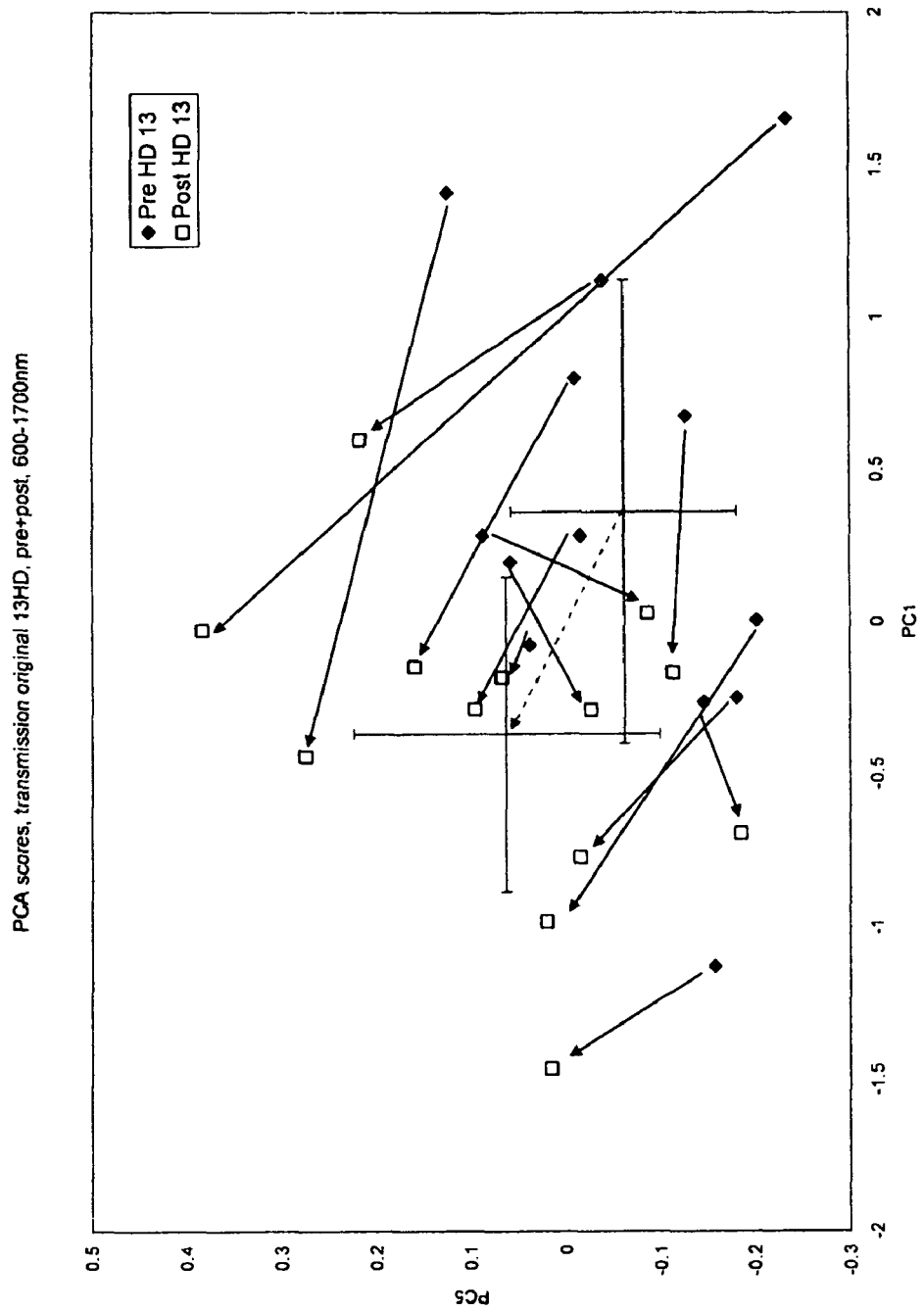
FIG. 8 is a PCA score plot using two PC's from spectra obtained from 13 pre- and post-hemodialysis patients.

This is useful, because when all 26 original spectra are plotted in terms of these two PCs (score plot), we get the distribution shown in FIG. 8. The centroids (±SD) are given as well as the average direction of shift with treatment (decreasing PC1, increasing PC5). Of the 13 patients, all 13 had decreasing PC1 after treatment, and 10 out of 13 had increasing PC5. For Patients 8, 10, and 13 PC5 decreased after treatment.

The PCs from the above analysis can be considered as the basis vectors defining the independent sources of variation in whole blood spectra across patients and treatments.

Figure 9:
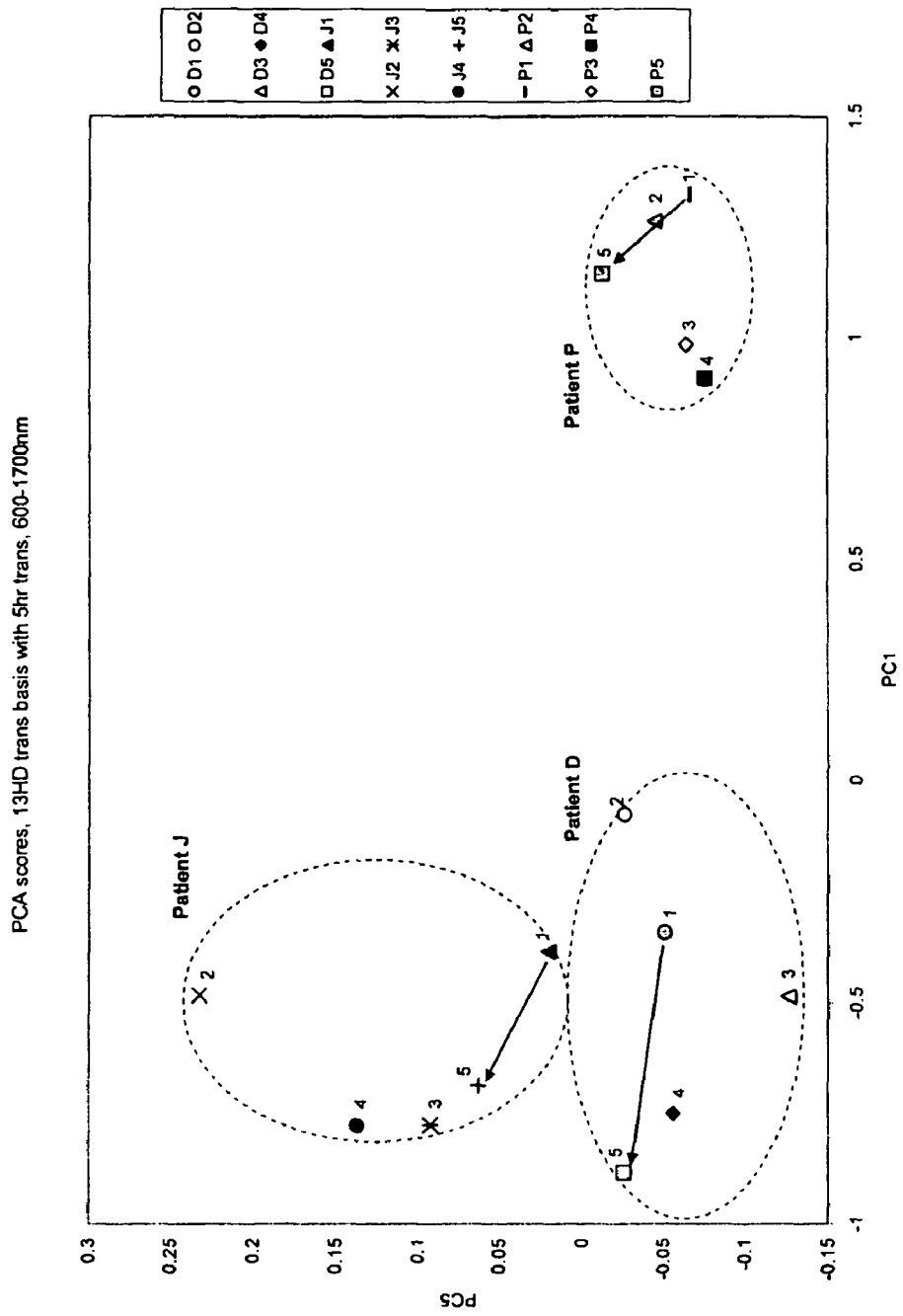
FIG. 9 is a PCA score plot obtained by projecting transmission spectra obtained from three hemodialysis patients on the basis eigenvector space defined by results from the 13 hemodialysis patients (FIG. 8).

If the transmission spectra obtained from the 3 HD patients (from Example 4, above) are projected onto the basis vector space defined by the 13 HD patients, and the results are expressed in terms of PC1 and PC5 scores alone, the score plot shown in FIG. 9 is obtained.

The scores for each patient are co-located and are separate from each other. The net direction of change with treatment is given by the arrows, and for all 3 patients this follows the general rule of decrease in PC1 and increase in PC5 with treatment.

It is interesting to note, however, the evolution of treatment at 1-hour intervals. There is certainly not a simple relationship to predict the state of the blood at intermediate points during treatment. While for all hourly samples Patient J maintained the same direction, this was not the case for the others.

Patients D and P changed direction in a complex way, but the net final direction was similar.

The use of PC1 and PC5 gives us a means to investigate changes in patients as a result of their treatment. The technique may also be used to monitor patient blood or tissue over multiple treatments and in the short and long-term. Anomalies and trends in the spectral indices observed within patients and across a patient group may lead to the development of indicators of presence, progression, treatment, and outcome of a clinical condition. The use of two different light-tissue interaction techniques in the development of spectrally-derived indices (in this case, diffuse reflection to assess the level of a potential source of interference and transmission to represent the clinical condition) is beneficial.

Example 5

Monitoring Disease Progression and Treatment

Figure 10:
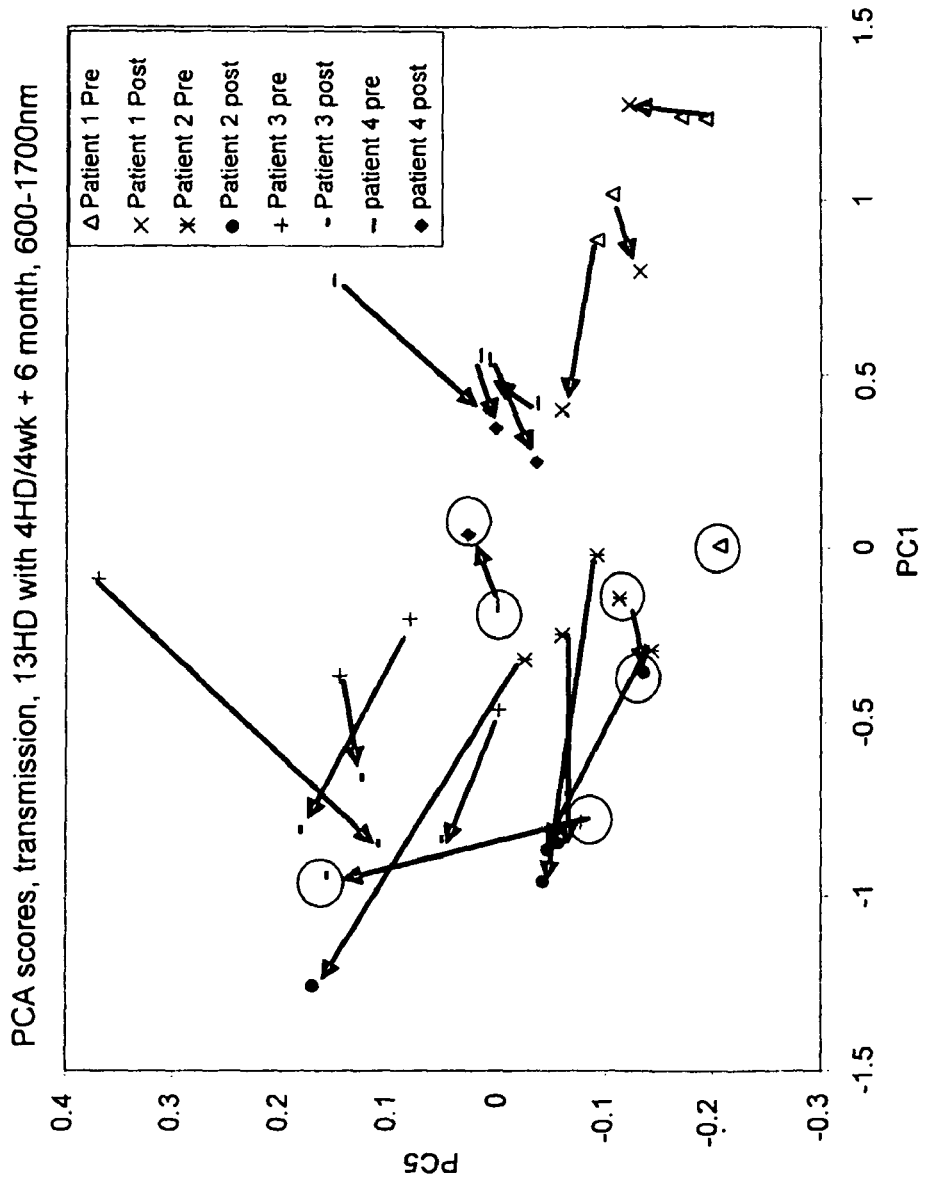
FIG. 10 depicts is a PCA score plot obtained by projecting transmission spectra obtained from three hemodialysis patients over time on the basis eigenvector space defined by results from the 13 hemodialysis patients (FIG. 8).

To illustrate the concept of monitoring patients over multiple treatments to assess the progression of a disease or longer-term impact of treatment, four HD patients were recruited. Blood samples pre- and post-dialysis were taken from each patient on one Thursday treatment, and this was repeated for the following three Thursdays. The four patients were then followed up six months later, with a pre- and post-dialysis blood sample again taken from a regular Thursday HD treatment session. The transmission spectra from these blood samples were then projected onto the PCA basis created from the 13 HD patients as described above, and the principal component scores for PC1 and PC5 for these patients were plotted. The result is given in FIG. 10, where the arrows connect pre-to-post for a single treatment, and the circles indicate the 6-month follow-up scores.

Besides each patient having pre- and post-hemodialysis data grouped together, 15 out of 18 treatments had decreasing PC1, and 11 out of 18 treatments had increasing PC5. This was still the predominant treatment direction.

More variety is apparent in the direction of treatment, although where increasing PC1 occurred (3 cases) the magnitude of the increase was small. When PC5 decreased (7 cases), the magnitude was sometimes large. One direction seems to be forbidden in all patients thus far: increasing PC1 and decreasing PC5.

Patient 1 had anomalies: increasing PC1 and decreasing PC5 in separate weeks. Patient 4 had anomalous data every time: either increasing PC1 or decreasing PC5.

From these spectral indices it is apparent that dialysis treatments, even in consecutive weeks in the same patient, may differ substantially in terms of their impact in altering the light interaction properties of the blood. Also note that for Patients 1 and 4, 6-month pre-dialysis PC1 scores deviated substantially from the 4-week baseline values.

The indices presented provide a means to monitor short and long-term changes in patients that may be associated with their state of health and may correlate to eventual clinical outcomes. These indices were derived by means of combining diffuse reflection data (to quantify the level of interference from oxygen saturation and allow suitable parameters to be chosen to minimize this source of interference) with transmission data (containing the spectral information indicative of the clinical condition).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES 1. 2001 Report, Vol. 1: Dialysis and Renal Transplantation, Canadian Organ Replacement Register, Canadian Institute for Health Information, Ottawa, August 2001.
2. P. S. Jensen, J. Bak, S. Ladefoged, and S. Andersson-Engels, "Determination of urea, glucose, and phosphate in dialysate with Fourier transform infrared spectroscopy," *Spectrochim. Acta., Part A* 60, 899-905 (2004).
3. R. Vanholder, G. Glorieux, R. de Smet, and N. Lameire, "New insights in uremic toxins," *Kidney Int.* 63, supplement 84, S6-S10 (2003).
4. R. Vanholder, A. Argiles, U. Baurmeister et al., "Uremic toxicity: present state of the art," *Int. J. Artif. Organs* 24, 695-725 (2001).
5. P. S. Jensen, J. Bak, S. Ladefoged, S. Andersson-Engels, and L. Friis-Hansen, "Online monitoring of urea concentration in dialysate with dual-beam Fourier transform near-infared spectroscopy," *J. Biomed. Opt.* 9(3), 553-557 (2004).
6. C. V. Eddy and M. A. Arnold, "Near-infrared spectroscopy for measuring urea in hemodialysis fluids," *Clin. Chem.* 47(7), 1279-1286 (2001).
7. J. T. Olesberg, M. A. Arnold, and M. J. Flanigan, "Online measurement of urea concentration in spent dialysate during hemodialysis," *Clin. Chem.* 50(1), 175-181 (2004).
8. E. Mancini, A. Santoro, M. Spongano, F. Paolini, M. Rossi, and P. Zucchelli, "Continuous on-line optical absorbance recording of blood volume changes during hemodialysis," *Artif. Organs* 17(8), 691-694 (1993).
9. J. P. M. de Vries, C. G. Olthof, V. Visser, P. M. Kouw, A. van Es, A. J. M. Donker, and P. M. J. M. de Vries, "Continuous measurement of blood volume during hemodialysis by an optical method," *ASAIO J.* 38, M181-185 (1992).
10. R. R. Steuer, D. A. Bell, and L. L. Barrett, "Optical measurement of hematocrit and other biological constituents in renal therapy," *Adv. Renal Repl. Ther.* 6(3), 217-224 (1999).
11. W. Petrich, B. Dolenko, J. Fruh et al., "Disease pattern recognition in infrared spectra of human sera with diabetes mellitus as an example," *Appl. Opt.* 39(19), 3372-3379 (2000).
12. Z. Ge, K. T. Schomacker, and N. S. Nishioka, "Identification of colonic dysplasia and neoplasia by diffuse reflectance spectroscopy and pattern recognition techniques," *Appl. Spectrosc.* 52(6), 833-839 (1998).
13. B. K. Lavine, C. E. Davidson, A. J. Moores, "Genetic algorithms for spectral pattern recognition," *Vibr. Spectrosc.* 28, 83-95 (2002).
14. W. Lin, X. Yuan, P. Yuen, W. I. Wei, J. Sham, P. Shi, and J. Qu, "Classification of in vivo autofluorescence spectra using support vector machines," *J. Biomed. Opt.* 9(1), 180-186 (2004).
15. R. C. Schneider, K. A. Kovar, "Analysis of ecstasy tablets: comparison of reflectance and transmittance near infrared spectroscopy," *Forensic Sci. Int.* 134, 187-195 (2003).

16. S. Prahl, "Optical absorption of hemoglobin," http://omlc.ogi.edu/spectra/hemoglobin/.
17. G. M. Hale and M. R. Querry, "Optical constants of water in the 200 nm to 200 μm wavelength region," *Appl. Opt.* 12(3), 555-563 (1973).
18. I. A. Cowe and J. W. McNicol, "The use of principal components in the analysis of near-infrared spectra," *Appl. Spectrosc.* 39(2), 257-266 (1985).
19. G. A. Martinez and R. Bragos, "On-line measurement of urea in blood using optical spectroscopy in the visible range; validation of the cell shrinkage hypothesis," *IEEE Instrumentation and measurement technology conference ITMC* 2004, Como, Italy, 1966-1969 (2004).
20. B. R. Soller, J. Favreau, and P. O. Idwasi, "Investigation of electrolyte measurement in diluted whole blood using spectroscopic and chemometric methods," *Appl. Spectrosc.* 57(2), 146-151 (2003).
21. Y. J. Kim, S. Kim, J. W. Kim, and G. Yoon, "Data preprocessing and partial least squares regression analysis for reagentless determination of hemoglobin concentrations using conventional and total transmission spectroscopy," *J. Biomed. Opt.* 6(2), 177-182 (2001).
22. A. S. Goldfarb-Rumyantzev, M. H. Schwenk, S. Liu, E. Wrone, and J. K. Leypoldt, "New empiric expressions to calculate single pool Kt/V and equilibrated Kt/V," *ASAIO J* 48(5), 570-576 (2002).
23. L. Gabutti, N. Ferrari, G. Giudici, G. Mombelli, and C. Marone, "Unexpected haemodynamic instability associated with standard bicarbonate haemodialysis," *Nephrol. Dial. Transplant* 18(11), 2369-2376 (2003).
24. M. K. Alam, M. R. Rohrscheib, J. E. Franke, T. M. Niemczyk, J. D. Maynard, and M. R. Robinson, "Measurement of pH in whole blood by near-infrared spectroscopy," *Appl. Spectrosc.* 53(3), 316-324 (1999).
25. N. A. Rosen, W. E. Charash, and E. F. Hirsch, "Near-infrared spectrometric determination of blood pH," *J. Surg. Res.* 106(2), 282-286 (2002).
26. I. Valyi-Nagy, K. J. Kaffka, J. M. Jako, E. Gonczol, and G. Domjan, "Application of near infrared spectroscopy to the determination of haemoglobin," *Clin. Chim. Acta* 264, 117-125 (1997).
27. J. T. Kuenstner, K. H. Norris, and W. F. McCarthy, "Measurement of hemoglobin in unlysed blood by near-infrared spectroscopy," *Appl. Spectrosc.* 48(4), 484-488 (1994).

The embodiments of the invention in which an exclusive property or privilege is claimed are defined as follows:

1. A method for investigating a clinical condition of a subject, comprising the steps of:
   (a) measuring spectral properties of bodily fluid or tissue of said subject using one or more spectrometers to measure at least two optical properties; and
   (b) correlating the spectral properties to a corresponding clinical condition,
   wherein the at least two optical properties are independently selected from the group consisting of diffuse reflection, inelastic (Raman) scattering, absorption/transmission, and fluorescence, and
   wherein said spectral properties are measured using radiation at ultra-violet wavelengths, visible wavelengths, near-infrared wavelengths, mid-infrared wavelengths or a combination thereof.

2. The method of claim 1, wherein said correlation step includes deriving from the measured spectral properties an index or indices correlating with the clinical condition of said subject at a single point in time, over a period of time, quasi-continuously or continuously, in response to at least one effector.

3. The method of claim 2, wherein said at least one effector is a single treatment, multiple treatments, a single dose of a medicine or multiple doses of a medicine.

4. The method of claim 2, wherein said clinical condition is indicative of long-term health of the subject, subjective or objective clinical outcome in said subject, or a potential future change in clinical status or state of health of said subject.

5. The method of claim 4, wherein said potential future change in clinical status or state of health of said subject is a predisposition to disease.

6. The method of claim 1, further comprising the step of comparing the measured spectral properties to spectral properties obtained from a population of subjects using said at least two optical techniques, wherein said population of subjects has a known clinical condition.

7. The method of claim 1, wherein the clinical condition is a disease state.

8. The method of claim 1, wherein the bodily fluid is whole blood or blood serum.

9. The method of claim 1, further comprising the step of processing raw spectral data to obtain said measured spectral properties.

10. The method of claim 9, wherein said processing step comprises one or more of the following:
    (a) normalizing raw spectral data relative to a spectral data obtained from a baseline sample;
    (b) normalizing raw spectral data relative to total integrated power;
    (c) combining chosen spectral bands and aggregating spectral data obtained using said at least two optical properties;
    (d) applying a spectral pretreatment correction; and
    (e) applying a chemometric algorithm.

11. The method of claim 10, wherein said spectral pretreatment correction is baseline correction, standard normal variate transformation, multiple scatter correction, wavelength selection, smoothing, derivatisation, or any combination thereof.

12. The method of claim 10, wherein said chemometric algorithm is a principal component analysis.

13. A method of monitoring changes in a clinical condition of a subject, comprising the steps of:
    (a) measuring spectral changes in bodily fluid or tissue of said subject using one or more spectrometers to measure and at least two optical properties; and
    (b) correlating the measured changes to a change in clinical condition,
    wherein the at least two optical properties are independently selected from the group consisting of diffuse reflection, inelastic (Raman) scattering, absorption/transmission, and fluorescence, and
    wherein said spectral changes are measured using radiation at ultra-violet wavelengths, visible wavelengths, near-infrared wavelengths, mid-infrared wavelengths or a combination thereof.

14. The method of claim 13, wherein said correlation step includes deriving from the measured spectral properties an index or indices correlating with the clinical condition of said subject.

15. The method of claim 13, further comprising the step of comparing the measured spectral properties over time.

16. The method of claim 15, wherein said comparison step includes a comparison to baseline spectral properties obtained at an initial time point.

17. The method of claim 13, wherein the bodily fluid is whole blood or blood serum.

18. The method of claim 13, further comprising the step of processing raw spectral data to obtain said measured spectral changes.

19. The method of claim 18, wherein said processing step comprises one or more of the following:
   (a) normalizing raw spectral data relative to a spectral data obtained from a baseline sample;
   (b) normalizing raw spectral data relative to total integrated power;
   (c) combining chosen spectral bands and aggregating spectral data obtained using said at least two optical properties;
   (d) applying a spectral pretreatment correction; and
   (e) applying a chemometric algorithm.

20. The method of claim 19, wherein said spectral pretreatment correction is baseline correction, standard normal variate transformation, multiple scatter correction, wavelength selection, smoothing, derivitisation, or any combination thereof.

21. The method of claim 19, wherein said chemometric algorithm is a principal component analysis.

22. The method of claim 13, wherein the method is used to monitor disease progression, onset, regulation or treatment in said subject or to monitor changes in athletic conditioning or performance of said subject.

23. A method for deriving an index or indices for correlation to an observed clinical condition of a subject comprising the steps of
   (a) obtaining a body of raw spectral data by measuring spectral properties of bodily fluid or tissue of said subject using one or more spectrometers to measure at least two optical techniques properties; and
   (b) comparing the raw spectral data with the clinical condition of said subject,
wherein the at least two optical properties are independently selected from the group consisting of diffuse reflection, inelastic (Raman) scattering, absorption/transmission, and fluorescence.

24. A method for overcoming confounding or interfering influences on measured optical spectra by obtaining, using one or more spectrometer, a body of raw spectral data from measured spectral properties of a bodily fluid or tissue of a subject using at least two optical properties, wherein the at least two optical properties are independently selected from the group consisting of diffuse reflection, inelastic (Raman) scattering, absorption/transmission, and fluorescence.

25. The method of claim 24, wherein said confounding or interfering influences are oxygen saturation, hematocrit, hemoglobin, heparin, pH, environmental factors, temperature, humidity, or a combination thereof.

* * * * *

UNITED STATES PATENT AND TRADEMARK OFFICE
CERTIFICATE OF CORRECTION

| | | |
|---|---|---|
| PATENT NO. | : 8,125,623 B2 | |
| APPLICATION NO. | : 12/383930 | |
| DATED | : February 28, 2012 | |
| INVENTOR(S) | : Rejean Munger and Neil Lagali | |

It is certified that error appears in the above-identified patent and that said Letters Patent is hereby corrected as shown below:

In the Claims:
Column 28, claim 23, line 7: After "two optical" delete "techniques"

Signed and Sealed this
Seventeenth Day of April, 2012

David J. Kappos
*Director of the United States Patent and Trademark Office*